United States Patent
Kling et al.

(10) Patent No.: US 7,625,896 B2
(45) Date of Patent: Dec. 1, 2009

(54) PYRIDYLSULFONAMIDE DERIVATIVES

(75) Inventors: Lothar Kling, Mannheim (DE); Ulrike Reiff, Penzberg (DE); Manfred Schwaiger, Wang-Bergen (DE); Georg Tiefenthaler, Sindelsdorf (DE); Wolfgang von der Saal, Murnau (DE); Thomas von Hirschheydt, Penzberg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 23 days.

(21) Appl. No.: 11/594,297

(22) Filed: Nov. 8, 2006

(65) Prior Publication Data
US 2007/0123513 A1 May 31, 2007

(30) Foreign Application Priority Data
Nov. 25, 2005 (EP) ................................. 05025733

(51) Int. Cl.
| | |
|---|---|
| A61K 31/535 | (2006.01) |
| C07D 413/00 | (2006.01) |
| A61K 31/445 | (2006.01) |
| C07D 211/68 | (2006.01) |
| C07D 401/00 | (2006.01) |
| A61K 31/44 | (2006.01) |

(52) U.S. Cl. ................... 514/237.2; 544/124; 546/194; 546/276.4; 514/318; 514/343

(58) Field of Classification Search ................ 546/255, 546/268.1, 194, 276.4; 514/277, 336, 318, 514/343, 237.2; 544/106, 124
See application file for complete search history.

(56) References Cited

U.S. PATENT DOCUMENTS

| | | | |
|---|---|---|---|
| 3,991,057 A | 11/1976 | Delarge et al. | |
| 4,018,929 A | 4/1977 | Delarge et al. | |

FOREIGN PATENT DOCUMENTS

| | | | |
|---|---|---|---|
| WO | 02098848 | * | 12/2002 |
| WO | WO 02/098848 | | 12/2002 |
| WO | WO 03/035629 | | 5/2003 |
| WO | WO 2004/048329 | | 6/2004 |

OTHER PUBLICATIONS

Hcaplus 138:24539.*
Patani et. al., "Bioisosterism: A Rational Approach in Drug Design", Chem. Rev., 96 (8), 3147 -3176, 1996. cr950066q S0009-2665(95)00066-5.*
Patani et. al., "Bioisosterism: A Rational Approach in Drug Design", Chem. Rev., 96 (8), 3147-3176, 1996, cr950066q S0009-2665 (95)0066-5.*
Hcaplus 138:24539, "Preparation of benzoylsulfonamide and sulfonylbenzamidine angiogenesis inhibitors for use as antitumor agents", Corbett et. al. WO 2002098848.*
Suggitt et. al., "50 Years of Preclinical Anticancer Drug Screening: Empirical to Target-Driven Approaches", vol. 11, 971-981, Feb. 1, 2005, Clinical Cancer Research, pp. 971-981.*
Johnson et. al., "Relationships between drug activity in NCI preclinical in vitro and in vivo models and early clinical trials", British Journal of Cancer, (2001) 84 (10), 1424-1431.*
Owa et al., Bioorg. Med. Chem. Lett., 12(16), pp. 2097-2100 (2002).
Corey et al., J. Org. Chem., 54, pp. 389-393 (1989).
Bastin et al., Organic Proc. Res. Dev., 4, pp. 427-435 (2000).
Delarge et al., Annales Pharmaceutiques Francaises, 41, pp. 55-60 (1983).

* cited by examiner

*Primary Examiner*—Janet L Andres
*Assistant Examiner*—Binta M Robinson
(74) *Attorney, Agent, or Firm*—George W. Johnston; Patricia S. Rocha-Tramaloni; Gene J. Yao

(57) ABSTRACT

The present invention relates to the compounds of formula I:

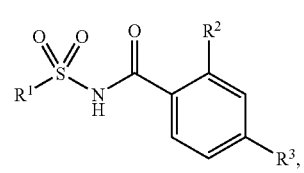

formula I their pharmaceutically acceptable salts, enantiomeric forms, diastereoisomers and racemates, the preparation of such compounds, pharmaceutical compositions containing them and their manufacture, as well as the use of such compounds in the control or prevention of illnesses such as cancer.

12 Claims, No Drawings

PYRIDYLSULFONAMIDE DERIVATIVES

PRIORITY TO RELATED APPLICATIONS

This application claims the benefit of European Application No. 05025733.6, filed Nov. 25, 2005, which is hereby incorporated by reference in its entirety.

The present invention relates to novel pyridylsulfonamide derivatives, to a process for their manufacture, pharmaceutical compositions containing them and their manufacture as well as the use of these compounds as pharmaceutically active agents.

BACKGROUND OF THE INVENTION

The treatment of cancer diseases is of great importance in medicine. There is a worldwide need for effective cancer therapies in order to achieve a treatment which is appropriate to a patient and is target-orientated. This can be seen in the large number of scientific studies which have recently appeared in the fields of applied oncology and fundamental research relating to cancer therapy. The effects of tumor inhibitors are due to a very wide variety of mechanisms, only some of which are known. It is not unusual for known tumor drugs to be found to have new mechanisms of action. This is also to be expected in the case of the compounds according to the invention. Many tumor drugs act by way of mechanisms such as blockading the mechanism of cell division in the cell, preventing the tumor from being supplied with nutrients and oxygen (antiangiogenesis), preventing metastasis, preventing the reception and the onward transmission of growth signals to the tumor cell or forcing the tumor cell into programmed cell death (apoptosis).

Because they have different mechanisms of action, including interacting with different intracellular targets, the clinically relevant cytostatic agents are frequently administered in combination in order to achieve a synergistic therapeutic effect.

Delarge, J., et al, Annales Pharmaceutiques Francaises 41 (1983) 55-60, describes some 4-phenylthiopyridine-3-sulfonamides with hypolipemic properties. U.S. Pat. No. 4,018,929 relates to pyridinesulfonamides as inflammation inhibitors and diuretics. Owa, T.; et al, Bioorg Med Chem Lett (2002), 12(16), 2097-2100 relates to N-(7-indolyl)-3-pyridinesulfonamide derivatives as antitumor agents.

WO 2003/035629 relates to thiophene- and thiazole-sulfonamides as antineoplastic agents. WO 02/098848 and WO 2004/048329 relate to benzoylsulfonamides as antitumor agents.

SUMMARY OF THE INVENTION

The present invention relates to pyridylsulfonamides of the general formula I and all pharmaceutically acceptable salts thereof wherein formula I is:

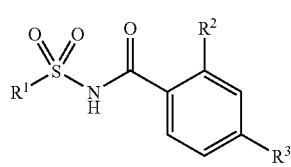

formula I wherein:

$R^1$ is pyridyl which is optionally substituted one to three times by a substituent selected from the group consisting of:
(a) —O-phenyl, wherein the phenyl is substituted one to two times by halogen, cyano, alkyl, alkoxy, nitro, amino, alkylamino or dialkylamino;
(b) —NRR', wherein R and R' independently represent hydrogen or alkyl; or alternatively R and R' form together with the nitrogen atom to which they are attached, a saturated 5 to 7 membered heterocycle which is optionally substituted one to three times by alkyl or alkoxy;
(c) halogen; and
(d) alkyl;

$R^2$ is fluorine, chlorine, bromine, methyl, methoxy or trifluoromethyl; and $R^3$ is fluorine, chlorine, bromine, methyl or trifluoromethyl.

The compounds according to this invention show antiproliferative activity and inhibit the growth of tumor cells in vitro and in vivo. The present invention provides the compounds of formula I and their tautomers, pharmaceutically acceptable salts, enantiomeric forms, diastereoisomers and racemates. The present invention also provides methods of using such compounds for the inhibition of tumor growth; methods of preparing or manufacturing such compounds; pharmaceutical compositions containing such compounds and their manufacture; as well as the use of the above-mentioned compounds in the control or prevention of illnesses, disorders, diseases, and/or conditions such as cancer including colorectal cancer, breast cancer, lung cancer, prostate cancer, pancreatic cancer, gastric cancer, bladder cancer, ovarian cancer, melanoma, neuroblastoma, cervical cancer, kidney or renal cancer, leukemias and lymphomas.

DETAILED DESCRIPTION OF THE INVENTION

1. Definitions

The term "alkyl" as used herein means a saturated, straight-chain or branched-chain hydrocarbon containing from 1 to 6 carbon atoms, preferably 1 to 4 carbon atoms, such as methyl, ethyl, n-propyl, isopropyl, n-butyl, 2-butyl, t-butyl, n-pentyl, or n-hexyl.

The term "alkoxy" as used herein means an alkyl group as defined above which is attached via an oxygen (—O—). Examples include methoxy, ethoxy, isopropoxy, n-butoxy, 1-methyl-propoxy, 2-methyl-propoxy and the like.

The term "alkylamino" as used herein means an alkyl-NH— group wherein the alkyl is defined as above. Examples include N-methyl-amino, N-ethyl-amino, N-isopropyl-amino, N-(2-methyl-prop-1-yl)-amino and the like.

The term "dialkylamino" as used herein means an (alkyl)$_2$N— group wherein the two alkyl groups are independently defined as above. Examples include N,N-dimethylamino, N-ethyl-N-methyl-amino, N,N-diethylamino and the like.

The term "halogen" as used herein means fluorine, chlorine, bromine or iodine. In preferred embodiments the halogen is fluorine, chlorine or bromine and more preferably chlorine or bromine.

The term "heterocycle" which is formed by R an R' together with the nitrogen atom to which R and R' are attached, means a saturated, monocyclic ring with 5 to 7 ring atoms which contains up to 3, preferably 1 or 2 heteroatoms wherein at least one heteroatom is nitrogen and the remaining heteroatoms are selected independently from the group consisting of nitrogen, oxygen and sulfur, and wherein the remaining ring atoms are carbon atoms. Examples of such saturated heterocycles include pyrrolidine, morpholine, piperazine and N-methyl-piperazine, piperidine, oxazolidine, thiazolidine, azepane and the like. In preferred embodiments the heterocycle is morpholine, thiomorpholine, pyrrolidine or azepane, and more preferably morpholine. According to the definition of formula I, such heterocycles can be optionally substituted one to three times by alkyl or alkoxy. Preferably such heterocycles can be optionally substituted one to three times by $(C_1-C_3)$-alkyl or $(C_1-C_3)$-alkoxy and more preferably such heterocycles can be optionally substituted once or twice by methyl or methoxy The term "pyridyl" as used herein means pyrid-2-yl, pyrid-3-yl or pyrid-4-yl. In preferred embodiments the pyridyl is pyrid-2-yl or pyrid-3-yl and more preferably pyrid-3-yl. If such pyridyl is substituted, it is substituted one to three times, preferably one or two times. The preferred position of the substituents is ortho to the position of the N-atom of the pyridyl residue, e.g. the 6-position of pyrid-2-yl, the 2- or 6-position (preferably the 6-position) of pyrid-3-yl and the 2- or 6-position of pyrid-4-yl. Another preferred position of the substituents of the pyrid-2-yl and pyrid-3-yl is para to the pyridyl-$S(O)_2$— bond.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The compounds according to the present invention may exist in the form of their pharmaceutically acceptable salts. As used herein, the term "pharmaceutically acceptable salt" refers to conventional acid-addition salts that retain the biological effectiveness and properties of the compounds of formula I and are formed from suitable non-toxic organic or inorganic bases or, if the compounds of formula I contain a basic group in $R^1$, from organic or inorganic acids. Examples of base-addition salts include those derived from sodium, potassium, ammonium, quaternary ammonium hydroxides (such as for example, tetramethylammonium hydroxide), especially from sodium. Examples of acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. The chemical modification of a pharmaceutical compound (i.e. a drug) into a salt is a technique well known to pharmaceutical chemists to obtain improved physical and chemical stability, hygroscopicity, flowability and solubility of compounds. See e.g. Stahl, P. H., and Wermuth, G., (editors), Handbook of Pharmaceutical Salts, Verlag Helvetica Chimica Acta (VHCA), Zürich, (2002) or Bastin, R. J., et al., Organic Proc. Res. Dev. 4 (2000) 427-435.

In relation to the processes described herein for the preparation of the compounds of the present invention, the term "activated before" means that the carboxylic acid group is converted into a reactive carboxylic acid derivative before the reaction. Such activation is typically carried out without solvent, or in solvents like dichloromethane, dichloroethane, tetrahydrofuran, dioxane and mixtures thereof, at temperatures between 0° C. and 100° C. Typical methods used for the activation are chlorination or formation of an imidazolide. Typically used chlorinating reagents are thionylchloride, oxalyl chloride, phosphorus trichloride, phosphorus pentachloride, phosphorus oxychloride, N-chlorosuccinamide triphenylphosphine. A typically used imidazolination method is the reaction with N,N'-carbonyl diimidazole (CDI). Other typically used activation methods include the use of activating agents such as 1-ethyl-3-(3'-dimethylaminopropyl)carbodiimide (EDCI), hydroxy-benzotriazole (HOBt) and the like.

As used herein, in relation to mass spectrometry (MS) the term "ESI+" refers to positive electrospray ionization mode.

2. Detailed Description

One embodiment of the invention are the compounds of formula I, wherein:

$R^1$ is pyridyl which is optionally substituted one to three times by a substituent selected from the group consisting of:

(a) —O-phenyl, wherein the phenyl is substituted one to two times by halogen, cyano, alkyl, alkoxy, nitro, amino, alkylamino or dialkylamino;

(b) —NRR', wherein R and R' independently represent hydrogen or alkyl; or alternatively R and R' form together with the nitrogen atom to which they are attached a saturated 5 to 7 membered heterocycle, which is optionally substituted one to three times by alkyl;

(c) halogen; and (d) alkyl; and $R^2$ is fluorine, chlorine, bromine, methyl or trifluoromethyl.

One embodiment of the invention are the compounds of formula I, wherein:

$R^1$ is pyrid-3-yl which is optionally substituted one to three times by a substituent selected from the group consisting of:

(a) —O-phenyl;

(b) —NRR', wherein R and R' form together with the nitrogen atom to which they are attached a saturated 5 to 7 membered heterocycle, which is optionally substituted one to three times by alkyl or alkoxy (preferably by alkyl); and
(c) halogen.

Another embodiment of the invention are the compounds of formula I, wherein $R^1$ is pyrid-2-yl.

Another embodiment of the invention are the compounds of formula I, wherein $R^1$ is pyrid-3-yl.

Another embodiment of the invention are the compounds of formula I, wherein $R^1$ is pyrid-4-yl.

Another embodiment of the invention are the compounds of formula I, wherein:
$R^1$ is pyridyl which is optionally substituted one to three times by a substituent selected from the group consisting of:
(a) —NRR', wherein R and R' independently represent hydrogen or alkyl; or alternatively R and R' form together with the nitrogen atom to which they are attached a saturated 5 to 7 membered heterocycle, which is optionally substituted one to three times by alkyl or alkoxy (preferably by alkyl); and
(b) halogen.

Another embodiment of the invention are the compounds of formula I, wherein $R^1$ is pyridyl which is optionally substituted once by —NRR', wherein:
R and R' independently represent hydrogen or alkyl (preferably alkyl); or alternatively R and R' form together with the nitrogen atom to which they are attached a saturated 5 to 7 membered heterocycle, which is optionally substituted one to three times (preferably once or twice) by alkyl or alkoxy (preferably by alkyl).

Another embodiment of the invention are the compounds of formula I, wherein $R^1$ is pyrid-3-yl which is substituted once by —NRR', wherein:
R and R' independently represent alkyl; or alternatively R and R' form together with the nitrogen atom to which they are attached a saturated 5 to 7 membered heterocycle, which is optionally substituted once or twice by alkyl or alkoxy.

Another embodiment of the invention are the compounds of formula I, wherein $R^1$ is pyridyl which is optionally substituted one to three times by —NRR', wherein:
R and R' form together with the nitrogen atom to which they are attached a saturated 5 to 7 membered heterocycle, which is optionally substituted one to three times by alkyl or alkoxy (preferably by alkyl).

Another embodiment of the invention are the compounds of formula I, wherein $R^1$ is pyrid-3-yl which is substituted once by —NRR', wherein R and R' form together with the nitrogen atom to which they are attached a saturated 5 to 7 membered heterocycle, which is optionally substituted once or twice by alkyl or alkoxy.

Another embodiment of the invention are the compounds of formula I, wherein $R^1$ is pyridyl which is optionally substituted one to three times by —O-phenyl.

Another embodiment of the invention are the compounds of formula I, wherein $R^1$ is pyrid-3-yl which is substituted once by —O-phenyl.

One embodiment of the invention are the compounds of formula I, wherein $R^1$ is pyridyl which is optionally substituted one to three times by halogen.

One embodiment of the invention are the compounds of formula I, wherein $R^1$ is pyrid-3-yl which is substituted once or twice by halogen.

Another embodiment of the invention are the compounds of formula I, wherein $R^2$ is chlorine, bromine, methyl or trifluoromethyl.

Another embodiment of the invention are the compounds of formula I, wherein $R^2$ is chlorine, bromine, methyl, methoxy or trifluoromethyl.

Another embodiment of the invention are the compounds of formula I, wherein $R^2$ is fluorine and $R^3$ is chlorine.
Such compounds, for example, may be selected from the group consisting of:
6-Morpholin-4-yl-pyridine-3-sulfonic acid 4-chloro-2-fluoro-benzoylamide; sodium salt; and
6-Phenoxy-pyridine-3-sulfonic acid 4-chloro-2-fluoro-benzoylamide; sodium salt.

Another embodiment of the invention are the compounds of formula I, wherein $R^2$ is fluorine and $R^3$ is bromine.
Such compounds, for example, may be selected from the group consisting of:
6-Phenoxy-pyridine-3-sulfonic acid 4-bromo-2-fluoro-benzoylamide; sodium salt;
6-Morpholin-4-yl-pyridine-3-sulfonic acid 4-bromo-2-fluoro-benzoylamide; sodium salt; and
5-Bromo-6-chloro-pyridine-3-sulfonic acid 4-bromo-2-fluoro-benzoylamide; sodium salt.

Another embodiment of the invention are the compounds of formula I, wherein $R^2$ is fluorine and $R^3$ is trifluoromethyl.
Such compounds, for example, may be selected from the group consisting of:
6-Morpholin-4-yl-pyridine-3-sulfonic acid 2-fluoro-4-trifluoromethyl-benzoylamide; sodium salt;
5-Bromo-6-chloro-pyridine-3-sulfonic acid 2-fluoro-4-trifluoromethyl-benzoylamide; sodium salt; and
6-Phenoxy-pyridine-3-sulfonic acid 2-fluoro-4-trifluoromethyl-benzoylamide; sodium salt.

Another embodiment of the invention are the compounds of formula I, wherein $R^2$ is chlorine and $R^3$ is chlorine.
Such compounds, for example, may be selected from the group consisting of:
6-Morpholin-4-yl-pyridine-3-sulfonic acid 2,4-dichloro-benzoylamide; sodium salt;
5-Bromo-6-chloro-pyridine-3-sulfonic acid 2,4-dichloro-benzoylamide; sodium salt;
Pyridine-3-sulfonic acid 2,4-dichloro-benzoylamide; sodium salt;
6-Phenoxy-pyridine-3-sulfonic acid 2,4-dichloro-benzoylamide; sodium salt;
4-Methoxy-3,4,5,6-tetrahydro-2H-[1,2']bipyridinyl-5'-sulfonic acid 2,4-dichloro-benzoylamide;
4-Methyl-3,4,5,6-tetrahydro-2H-[1,2']bipyridinyl-5'-sulfonic acid 2,4-dichloro-benzoylamide; ammonium salt;
6-Azepan-1-yl-pyridine-3-sulfonic acid 2,4-dichloro-benzoylamide;
6-Pyrrolidin-1-yl-pyridine-3-sulfonic acid 2,4-dichloro-benzoylamide;
6-Thiomorpholin-4-yl-pyridine-3-sulfonic acid 2,4-dichloro-benzoylamide;
3-Methyl-3,4,5,6-tetrahydro-2H-[1,2']bipyridinyl-5'-sulfonic acid 2,4-dichloro-benzoylamide;
6-(2,6-Dimethyl-morpholin-4-yl)-pyridine-3-sulfonic acid 2,4-dichloro-benzoylamide;
6-(Methyl-propyl-amino)-pyridine-3-sulfonic acid 2,4-dichloro-benzoylamide; and
6-((2S,6R)-2,6-Dimethyl-morpholin-4-yl)-pyridine-3-sulfonic acid 2,4-dichloro-benzoylamide.

Another embodiment of the invention are the compounds of formula I, wherein $R^2$ is chlorine and $R^3$ is fluorine.
Such compounds, for example, may be selected from the group consisting of:
6-Morpholin-4-yl-pyridine-3-sulfonic acid 2-chloro-4-fluoro-benzoylamide; sodium salt;

5-Bromo-6-chloro-pyridine-3-sulfonic acid 2-chloro-4-fluoro-benzoylamide; sodium salt;

6-Phenoxy-pyridine-3-sulfonic acid 2-chloro-4-fluoro-benzoylamide; sodium salt;

4-Methyl-3,4,5,6-tetrahydro-2H-[1,2']bipyridinyl-5'-sulfonic acid 2-chloro-4-fluoro-benzoylamide;

6-(Methyl-propyl-amino)-pyridine-3-sulfonic acid 2-chloro-4-fluoro-benzoylamide;

6-Azepan-1-yl-pyridine-3-sulfonic acid 2-chloro-4-fluoro-benzoylamide;

6-Pyrrolidin-1-yl-pyridine-3-sulfonic acid 2-chloro-4-fluoro-benzoylamide;

3-Methyl-3,4,5,6-tetrahydro-2H-[1,2']bipyridinyl-5'-sulfonic acid 2-chloro-4-fluoro-benzoylamide; and 6-Thiomorpholin-4-yl-pyridine-3-sulfonic acid 2-chloro-4-fluoro-benzoylamide.

Another embodiment of the invention are the compounds of formula I, wherein $R^2$ is chlorine and $R^3$ is bromine.

Such compounds, for example, may be selected from the group consisting of:

5-Bromo-6-chloro-pyridine-3-sulfonic acid 4-bromo-2-chloro-benzoylamide; sodium salt; and 6-Phenoxy-pyridine-3-sulfonic acid 4-bromo-2-chloro-benzoylamide; sodium salt.

Another embodiment of the invention are the compounds of formula I, wherein $R^2$ is bromine and $R^3$ is chlorine.

Such compounds, for example, may be selected from the group consisting of:

5-Bromo-6-chloro-pyridine-3-sulfonic acid 2-bromo-4-chloro-benzoylamide; sodium salt;

6-Morpholin-4-yl-pyridine-3-sulfonic acid 2-bromo-4-chloro-benzoylamide; sodium salt; and 6-Phenoxy-pyridine-3-sulfonic acid 2-bromo-4-chloro-benzoylamide; sodium salt.

Another embodiment of the invention are the compounds of formula I, wherein $R^2$ is bromine and $R^3$ is fluorine.

Such compounds, for example, may be selected from the group consisting of:

Pyridine-3-sulfonic acid 2-bromo-4-fluoro-benzoylamide; sodium salt 6-Morpholin-4-yl-pyridine-3-sulfonic acid 2-bromo-4-fluoro-benzoylamide; sodium salt;

5-Bromo-6-chloro-pyridine-3-sulfonic acid 2-bromo-4-fluoro-benzoylamide; sodium salt; and 6-Phenoxy-pyridine-3-sulfonic acid 2-bromo-4-fluoro-benzoylamide; sodium salt.

Another embodiment of the invention are the compounds of formula I, wherein $R^2$ is bromine and $R^3$ is methyl.

Such compounds, for example, may be selected from the group consisting of:

6-Morpholin-4-yl-pyridine-3-sulfonic acid 2-bromo-4-methyl-benzoylamide; sodium salt;

5-Bromo-6-chloro-pyridine-3-sulfonic acid 2-bromo-4-methyl-benzoylamide; sodium salt; and 6-Phenoxy-pyridine-3-sulfonic acid 2-bromo-4-methyl-benzoylamide; sodium salt.

Another embodiment of the invention are the compounds of formula I, wherein $R^2$ is methyl and $R^3$ is chlorine.

Such compounds, for example, may be selected from the group consisting of:

6-Morpholin-4-yl-pyridine-3-sulfonic acid 4-chloro-2-methyl-benzoylamide; sodium salt;

6-Phenoxy-pyridine-3-sulfonic acid 4-chloro-2-methyl-benzoylamide; sodium salt; and 5-Bromo-6-chloro-pyridine-3-sulfonic acid 4-chloro-2-methyl-benzoylamide; sodium salt.

Another embodiment of the invention are the compounds of formula I, wherein $R^2$ is methyl and $R^3$ is bromine.

Such compounds, for example, may be selected from the group consisting of:

6-Morpholin-4-yl-pyridine-3-sulfonic acid 4-bromo-2-methyl-benzoylamide; sodium salt;

5-Bromo-6-chloro-pyridine-3-sulfonic acid 4-bromo-2-methyl-benzoylamide; sodium salt; and 6-Phenoxy-pyridine-3-sulfonic acid 4-bromo-2-methyl-benzoylamide; sodium salt.

Another embodiment of the invention are the compounds of formula I, wherein $R^2$ is methyl and $R^3$ is methyl.

Such compounds, for example, may be selected from the group consisting of:

6-Morpholin-4-yl-pyridine-3-sulfonic acid 2,4-dimethyl-benzoylamide; sodium salt;

5-Bromo-6-chloro-pyridine-3-sulfonic acid 2,4-dimethyl-benzoylamide; sodium salt; and 6-Phenoxy-pyridine-3-sulfonic acid 2,4-dimethyl-benzoylamide; sodium salt.

Another embodiment of the invention are the compounds of formula I, wherein $R^2$ is trifluoromethyl and $R^3$ is fluorine.

Such compounds, for example, may be selected from the group consisting of:

Pyridine-3-sulfonic acid 4-fluoro-2-trifluoromethyl-benzoylamide; sodium salt;

6-Morpholin-4-yl-pyridine-3-sulfonic acid 4-fluoro-2-trifluoromethyl-benzoylamide; sodium salt;

6-Phenoxy-pyridine-3-sulfonic acid 4-fluoro-2-trifluoromethyl-benzoylamide; sodium salt;

5-Bromo-6-chloro-pyridine-3-sulfonic acid 4-fluoro-2-trifluoromethyl-benzoylamide; sodium salt;

4-Methyl-3,4,5,6-tetrahydro-2H-[1,2']bipyridinyl-5'-sulfonic acid 4-fluoro-2-trifluoromethyl-benzoylamide;

6-Azepan-1-yl-pyridine-3-sulfonic acid 4-fluoro-2-trifluoromethyl-benzoylamide;

6-Pyrrolidin-1-yl-pyridine-3-sulfonic acid 4-fluoro-2-trifluoromethyl-benzoylamide;

6-Thiomorpholin-4-yl-pyridine-3-sulfonic acid 4-fluoro-2-trifluoromethyl-benzoylamide; and 6-(Butyl-ethyl-amino)-pyridine-3-sulfonic acid 4-fluoro-2-trifluoromethyl-benzoylamide.

Another embodiment of the invention are the compounds of formula I, wherein $R^2$ is trifluoromethyl; and $R^3$ is trifluoromethyl.

Such compounds, for example, may be selected from the group consisting of:

5-Bromo-6-chloro-pyridine-3-sulfonic acid 2,4-bis-trifluoromethyl-benzoylamide; sodium salt;

6-Phenoxy-pyridine-3-sulfonic acid 2,4-bis-trifluoromethyl-benzoylamide; sodium salt;

6-Morpholin-4-yl-pyridine-3-sulfonic acid 2,4-bis-trifluoromethyl-benzoylamide; sodium salt; and Pyridine-3-sulfonic acid 2,4-bis-trifluoromethyl-benzoylamide; sodium salt.

Another embodiment of the invention are the compounds of formula I, wherein $R^2$ is trifluoromethyl and $R^3$ is chlorine.

Such compounds, for example, may be selected from the group consisting of:

4-Methyl-3,4,5,6-tetrahydro-2H-[1,2']bipyridinyl-5'-sulfonic acid 4-chloro-2-trifluoromethyl-benzoylamide;

6-Azepan-1-yl-pyridine-3-sulfonic acid 4-chloro-2-trifluoromethyl-benzoylamide;

6-Pyrrolidin-1-yl-pyridine-3-sulfonic acid 4-chloro-2-trifluoromethyl-benzoylamide; ammonium salt;

3-Methyl-3,4,5,6-tetrahydro-2H-[1,2']bipyridinyl-5'-sulfonic acid 4-chloro-2-trifluoromethyl-benzoylamide; ammonium salt;

4-Methoxy-3,4,5,6-tetrahydro-2H-[1,2']bipyridinyl-5'-sulfonic acid 4-chloro-2-trifluoromethyl-benzoylamide; ammonium salt;

6-(2,6-Dimethyl-morpholin-4-yl)-pyridine-3-sulfonic acid 4-chloro-2-trifluoromethyl-benzoylamide;

6-Dipropylamino-pyridine-3-sulfonic acid 4-chloro-2-trifluoromethyl-benzoylamide;

6-(Hexyl-methyl-amino)-pyridine-3-sulfonic acid 4-chloro-2-trifluoromethyl-benzoylamide; ammonium salt;

6-Thiomorpholin-4-yl-pyridine-3-sulfonic acid 4-chloro-2-trifluoromethyl-benzoylamide; ammonium salt;

6-(Ethyl-methyl-amino)-pyridine-3-sulfonic acid 4-chloro-2-trifluoromethyl-benzoylamide; ammonium salt;

6-(Methyl-propyl-amino)-pyridine-3-sulfonic acid 4-chloro-2-trifluoromethyl-benzoylamide; ammonium salt;

6-(Butyl-ethyl-amino)-pyridine-3-sulfonic acid 4-chloro-2-trifluoromethyl-benzoylamide; ammonium salt; and 6-((2R,6S)-2,6-Dimethyl-morpholin-4-yl)-pyridine-3-sulfonic acid 4-chloro-2-trifluoromethyl-benzoylamide.

Another embodiment of the invention are the compounds of formula I, wherein $R^2$ is methoxy and $R^3$ is chlorine.

Such compounds, for example, may be selected from the group consisting of:

4-Methoxy-3,4,5,6-tetrahydro-2H-[1,2']bipyridinyl-5'-sulfonic acid 4-chloro-2-methoxy-benzoylamide; sodium salt;

6-Thiomorpholin-4-yl-pyridine-3-sulfonic acid 4-chloro-2-methoxy-benzoylamide;

6-Pyrrolidin-1-yl-pyridine-3-sulfonic acid 4-chloro-2-methoxy-benzoylamide; ammonium salt;

6-Azepan-1-yl-pyridine-3-sulfonic acid 4-chloro-2-methoxy-benzoylamide; and

4-Methyl-3,4,5,6-tetrahydro-2H-[1,2']bipyridinyl-5'-sulfonic acid 4-chloro-2-methoxy-benzoylamide.

It will be understood that the above embodiments may be combined to form additional embodiments of the invention. Such combined embodiments are for example:

(a) One embodiment of the invention are the compounds of formula I, wherein $R^1$ is pyrid-2-yl and $R^2$ is chlorine, bromine, methyl or trifluoromethyl.

(b) One embodiment of the invention are the compounds of formula I, wherein:
  $R^1$ is pyrid-3-yl which is optionally substituted one to three times by a substituent selected from the group consisting of:
    (1) —O-phenyl;
    (2) —NRR', wherein R and R' form together with the nitrogen atom to which they are attached a saturated 5 to 7 membered heterocycle, which is optionally substituted one to three times by alkyl or alkoxy (preferably by alkyl); and
    (3) halogen; and
  $R^2$ is chlorine, bromine, methyl or trifluoromethyl.

(c) One embodiment of the invention are the compounds of formula I, wherein $R^1$ is pyrid-2-yl; $R^2$ is trifluoromethyl; and $R^3$ is fluorine.

(d) One embodiment of the invention are the compounds of formula I, wherein:
  $R^1$ is pyridyl which is optionally substituted one to three times by —NRR', wherein
  R and R' form together with the nitrogen atom to which they are attached a saturated 5 to 7 membered heterocycle, which is optionally substituted one to three times by alkyl or alkoxy (preferably by alkyl);
  $R^2$ is chlorine; and
  $R^3$ is chlorine.

(e) One embodiment of the invention are the compounds of formula I, wherein:
  $R^1$ is pyrid-3-yl which is optionally substituted one to three times by
    —NRR', wherein R and R' form together with the nitrogen atom to which they are attached a saturated 5 to 7 membered heterocycle, which is optionally substituted one to three times by alkyl or alkoxy (preferably by alkyl);
  $R^2$ is chlorine; and
  $R^3$ is chlorine.

(f) One embodiment of the invention are the compounds of formula I, wherein:
  $R^1$ is pyrid-3-yl; and
  $R^2$ is chlorine, bromine, methyl or trifluoromethyl.

(g) One embodiment of the invention are the compounds of formula I, wherein:
  $R^1$ is pyrid-3-yl which is substituted one to three times by —NRR',
    wherein R and R' form together with the nitrogen atom to which they are attached a saturated 5 to 7 membered heterocycle, which is optionally substituted one to three times by alkyl or alkoxy (preferably by alkyl); and
  $R^2$ is chlorine, methoxy or trifluoromethyl.

Another embodiment of the invention are the compounds of formula Ia and all pharmaceutically acceptable salts thereof wherein formula Ia is:

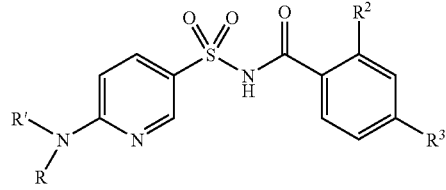

formula Ia wherein:
  R and R' independently represent hydrogen or alkyl (preferably alkyl); or alternatively R and R' form together with the nitrogen atom to which they are attached a saturated 5 to 7 membered heterocycle, which is optionally substituted one to three times (preferably once or twice) by alkyl or alkoxy;
  $R^2$ is fluorine, chlorine, bromine, methyl, methoxy or trifluoromethyl (preferably chlorine, bromine, methyl, methoxy or trifluoromethyl); and
  $R^3$ is fluorine, chlorine, bromine, methyl or trifluoromethyl.

Another embodiment of the invention are the compounds of formula Ia, wherein R and R' independently represent hydrogen or alkyl (preferably alkyl).

Another embodiment of the invention are the compounds of formula Ia, wherein R and R' form together with the nitrogen atom to which they are attached a saturated 5 to 7 membered heterocycle, which is optionally substituted one to three times (preferably once or twice) by alkyl or alkoxy.

Another embodiment of the invention are the compounds of formula Ia, wherein:
  R and R' form together with the nitrogen atom to which they are attached a saturated 5 to 7 membered heterocycle, which is optionally substituted one to three times (preferably once or twice) by alkyl or alkoxy; and R² is chlorine, bromine, methyl, methoxy or trifluoromethyl.

Another embodiment of the invention are the compounds of formula Ia, wherein:

R and R' form together with the nitrogen atom to which they are attached a saturated 5 to 7 membered heterocycle, which is optionally substituted one to three times (preferably once or twice) by alkyl or alkoxy;

R² is chlorine or trifluoromethyl; and

R³ is fluorine or chlorine.

The compounds of formula I may be prepared by any process known to be applicable to the preparation of chemically-related compounds. The present invention also provides methods of producing the compounds of formula I.

One embodiment of the invention is a process for the preparation of the compounds of formula I, by reacting a compound of formula III:

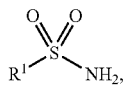

formula III wherein R¹ has the significance given for formula I, with a benzoic acid of formula IV:

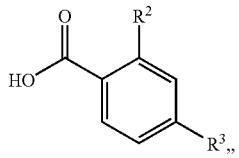

formula IV which is activated before and wherein R² and R³ have the significance given for formula I, to obtain the compounds of formula I,

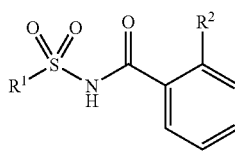

formula I wherein R¹, R² and R³ have the significance given for formula I.

The compounds of formula I, or pharmaceutically acceptable salt thereof, which are subject of the present invention, may be prepared by any process known to be applicable to the preparation of chemically-related compounds. Such processes, when used to prepare a compound of the formula I, or pharmaceutically-acceptable salt thereof, are illustrated by the following representative schemes 1 and 2 (and the examples) in which, unless otherwise stated, R, R', R¹, R² and R³ have the significance given herein before for formula I. Necessary starting materials are either commercially available or they may be obtained by standard procedures of organic chemistry. The preparation of such starting materials is, for example, described within the accompanying examples or in the literature cited below with respect to scheme 1. Alternatively necessary starting materials are obtainable by analogous procedures to those illustrated which are within the ordinary skill of an organic chemist.

Scheme 1

The pyridyl-sulfonamide derivatives of formula I can prepared starting, for example, from the corresponding sulfonamide chlorides as shown in scheme 1:

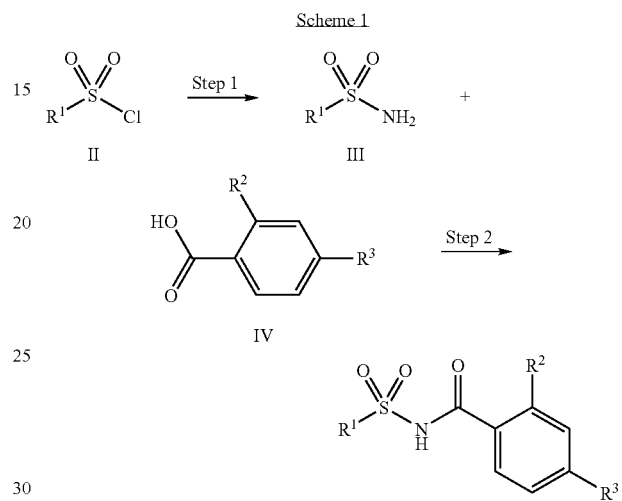

In scheme 1, R¹, R² and R³ have the significance given above for formula I.

Step 1: Step 1 of the reaction sequence (scheme 1) is a one step process in which a pyridine sulfonyl chloride of formula II is converted into a pyridine sulfonamide of formula III using methods well known to someone skilled in the art, e.g. ammonolysis. The reaction is typically carried out with or out without solvents such as dichloromethane, dichloroethane, acetonitrile, dioxane, tetrahydrofuran, dimethylformamide and mixtures thereof, at temperatures between −78° C. and 30° C. Pyridine sulfonyl chlorides of formula II are either commercially available or they can be prepared from the corresponding pyridine sulfonic acids by chlorination (see e.g. Corey, E. J.; et al, J. Org. Chem. 54 (1989) 389-393).

Alternatively to Step 1 (scheme 1), substituted pyridyl-3-sulfonamide derivatives of formula III, which are substituted at the 6-position with a nitrogen-containing heterocycles such as morpholine, thiomorpholine, pyrrolidine, piperidine, azepane and the like or with secondary amines such dimethylamino, diethylamine and the like, can be either prepared from 6-chloro-pyridyl-3-sulfonamide (via the 6-chloro-pyridyl-3-sulfonic acid chloride; see e.g. Naegeli, C.; et al, Helvetica Chimica Acta 21 (1938) 1746-1756; Owa, T.; et al, Bioorg Med Chem Lett (2002), 12(16), 2097-2100 or U.S. Pat. No. 3,991,057A) according to the procedures described in U.S. Pat. No. 3,991,057A; Thunus, L., Ann. Pharm. Fr. 32 (1974) 443-446; Thunus, L., Ann. Pharm. Fr. 35 (1977) 197-203; and Naegeli, C.; et al, Helvetica Chimica Acta 21 (1938) 1746-1756 or such derivates of formula III are commercially available. See also scheme 2. Step 2: Step 2 of the reaction sequence (scheme 1) is a two step process in which activation of the carboxylic group of the benzoic acid of formula IV is followed by acylation of the sulfonamide of formula III, to give the acylsulfonamide derivatives of formula I, using methods well known to someone skilled in the art. The first step (activation) is typically carried out with or without solvents (such as dichloromethane, dichloroethane, tetrahydrofuran, dioxane and mixtures thereof), at temperatures between 0° C. and 100° C. Typical methods used for the activation are chlorination or formation of an imidazolide. Typically used chlorinating reagents are thionyl chloride, oxalyl chloride, phosphorus trichloride, phosphorus pentachloride, phosphorus oxychloride and N-chlorosuccinimide with triphenylphosphine. A typically used imidazolination method is the reaction with N,N'-carbonyl diimidazole (CDI). Other typically used activation methods include the use of activating agents such as 1-(3-dimethylaminopropyl)-3-ethylcarbodiimide (EDCI) with or without hydroxy-benzotriazole (HOBt) and the like. The second step (acylation) is typically carried out in solvents such as dichloromethane, dichloroethane, acetonitrile, dioxane, tetrahydrofuran, chloroform, dimethylformamide and mixtures thereof, at temperatures between −10° C. and 100° C. Typically used bases are sodium hydride, potassium hydride, potassium carbonate, triethylamine, diisopropylethylamine, and (1,8-diazabicyclo[5.4.0]undec-7-ene (DBU).

Scheme 2

The substituted pyridyl-3-sulfonamide derivatives of formula I, which are substituted at the 6-position of the pyridyl with a nitrogen-containing heterocycles such as morpholine, thiomorpholine, pyrrolidine, piperidine, azepane and the like or with amines such dimethylamine, diethylamine and the like, are named Ia, and can be prepared according to the following scheme 2:

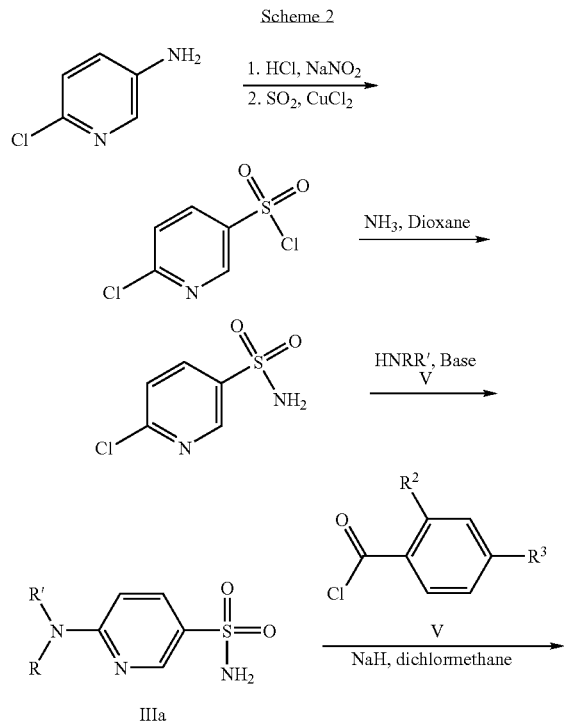

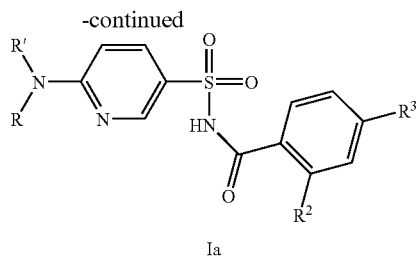

Ia

In scheme 2, $R^2$, $R^3$, R and R' have the significance given above for formula I.

The compounds of formula Ia in scheme 2 can be prepared via the 6-chloro-pyridyl-3-sulfonamide. 6-chloro-pyridyl-3-sulfonamide is either commercially available, or 6-chloro-pyridyl-3-sulfonamide can be prepared from 6-chloro-pyridin-3-ylamine via 6-chloro-pyridyl-3-sulfonic acid chloride following the first two steps of the reaction sequence in scheme 2; or alternatively 6-chloro-pyridyl-3-sulfonamide is prepared according to Naegeli, C.; et al, Helvetica Chimica Acta 21 (1938) 1746-1756 or U.S. Pat. No. 3,991,057.

6-chloro-pyridyl-3-sulfonamide is then reacted with the nitrogen-containing heterocycle or amine of formula IV, in the presence of a base like diisopropylethylamine, triethylamine, sodium hydride, potassium hydride, and DBU (1,8-diazabicyclo[5.4.0]undec-7-ene, in solvents such as dichloromethane, acetonitrile, dioxane, tetrahydrofuran, chloroform, dimethylformamide, N-methylpyrrolidone and mixtures thereof, at temperatures between −10° C. and 100° C., to give the compounds of formula IIIa.

In the final step the sulfonamides of formula IIIa are acylated by the benzoic acid chlorides of formula V (obtained from the benzoic acid of formula IV by chlorination—see details under step 2, scheme 1) to give the corresponding pyridyl-3-sulfonamide derivatives of formula Ia. The reaction is typically carried out in solvents such as dichloromethane, dichloroethane, acetonitrile, dioxane, tetrahydrofuran, chloroform, dimethylformamide and mixtures thereof, at temperatures between −10° C. and 100° C. Typically used bases are sodium hydride, potassium hydride, potassium carbonate, triethylamine, diisopropylethylamine, and (1,8-diazabicyclo[5.4.0] undec-7-ene (DBU).

The compounds of formula I can contain one or several chiral centers and can then be present in a racemic, a enantiomeric or diastereomeric form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

Pharmaceutical composition containing a compound of the present invention or a pharmaceutically acceptable salt thereof and a pharmaceutically acceptable carrier are also provided by the present invention, as is a process for their production, which comprises bringing one or more compounds of the present invention and/or pharmaceutically acceptable salts and, if desired, one or more other therapeutically valuable substances into a galenical administration form together with one or more pharmaceutically acceptable carriers.

An embodiment of the invention is a pharmaceutical composition, containing one or more compounds according to formula I, together with pharmaceutically acceptable carriers.

Another embodiment of the invention is a pharmaceutical composition, containing one or more compounds according to formula I, for the inhibition of tumor growth.

Another embodiment of the invention is a pharmaceutical composition, containing one or more compounds according to formula I, for the treatment of cancer.

Another embodiment of the invention is a pharmaceutical composition containing one or more compounds of formula I as active ingredients together with pharmaceutically acceptable carriers for the treatment of colorectal cancer, breast cancer, lung cancer, prostate cancer, pancreatic cancer, gastric cancer, bladder cancer, ovarian cancer, melanoma, neuroblastoma, cervical cancer, kidney or renal cancers, leukemias or lymphomas.

Another embodiment of the invention is the use of a compound according to formula I, for the manufacture of corresponding pharmaceutical compositions for the inhibition of tumor growth.

Another embodiment of the invention is the use of a compound according to formula I, for the manufacture of corresponding pharmaceutical compositions for the treatment of cancer. Another embodiment of the invention is the use of the compounds of formula I as anti-proliferating agents.

Another embodiment of the invention is the use of one or more compounds of formula I for the treatment of cancer.

Pharmacological Activity

The compounds of formula I and their pharmaceutically acceptable salts possess valuable pharmacological properties. It has been found that said compounds show anti-proliferative activity. Consequently the compounds of the present invention are useful in the therapy and/or prevention of proliferative diseases such as cancer. The activity of the present compounds as anti-proliferative agents is demonstrated by the following biological assay:

Viability Assay in HCT 116 Cells

A viability assay was performed using the CellTiter-Glo® Luminescent Cell Viability Assay (see Promega Corporation's Technical Bulletin No. 288, pp. 1-11 [revised February 2004] which is hereby incorporated by reference in its entirety). This assay is a homogeneous method of determining the number of viable cells in culture based on quantitation of the ATP present, an indicator of metabolically active cells. The assay is designed for use with multiwell formats, making it ideal for automated high-throughput screening (HTS), cell proliferation and cytotoxicity assays. The homogeneous assay procedure involves adding a single reagent (containing luciferase, luciferan substrate, and buffer) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The above-referenced assay generates a "glow-type" luminescent signal, produced by the luciferase reaction, which has a half-life generally greater than five hours, depending on cell type and medium used. The extended half-life eliminates the need to use reagent injectors and provides flexibility for continuous or batch mode processing of multiple plates. The unique homogeneous format avoids errors that may be introduced by other ATP measurement methods that require multiple steps.

HCT 116 cells (human colon carcinoma, ATCC-No. CCl-247) were cultivated in RPMI 1640 medium with GlutaMAX™ I (cell culture media that contains L-Alanyl-L-Glutamine [a stabilized form/source of L-Glutamine] from Invitrogen, Cat-No. 61870-010), 5% Fetal Calf Serum (FCS, Sigma Cat-No. F4135 (FBS)); 100 Units/ml penicillin/100 µg/ml streptomycin (=Pen/Strep from Invitrogen Cat. No. 15140). For the assay the cells were seeded in 384 well plates, 1000 cells per well, in the same medium. The next day the test compounds were added in various concentrations ranging from 30 µM to 0.0015 µM (10 concentrations, 1:3 diluted). After 5 days the viability assay was performed according to the instructions of the manufacturer. In brief: the cell-plate was equilibrated to room temperature for approximately 30 minutes and then the reagent (containing luciferase, luciferan substrate, and buffer) was added. The contents were carefully mixed for 15 minutes to induce cell lysis. After 45 minutes the luminescent signal was measured in Victor 2, (scanning multiwell spectrophotometer, Wallac).

Details:
  1st. Day:
    Medium: RPMI 1640 with GlutaMAX™ I (Invitrogen, Cat-No. 61870), 5% FCS (Sigma Cat.-No. F4135), Pen/Strep (Invitrogen, Cat No. 15140).
    HCT116 (ATCC-No. CCl-247): 1000 cells in 60 µl per well of 384 well plate (Greiner 781098, µClear-plate white)
    After seeding incubate plates 24 h at 37° C., 5% $CO_2$
  2nd. Day: Induction (Treatment with Compounds, 10 Concentrations):
    In order to achieve a final concentration of 30 µM as highest concentration 3.5 µl of 10 mM compound stock solution were added directly to 163 µl media. Then step e) of the dilution procedure described below, was followed.
    In order to achieve the second highest to the lowest concentrations, a serial dilution with dilution steps of 1:3 was followed according to the procedure (a-e) as described here below:
    a) for the second highest concentration add 10 µl of 10 mm stock solution of compound to 20 µl dimethylsulfoxide (DMSO)
    b) dilute 8×1:3 (always 10 µl to 20 µl DMSO) in this DMSO dilution row (results in 9 wells with concentrations from 3333.3 µM to 0.51 µM)
    c) dilute each concentration 1:47.6 (3.5 µl compound dilution to 163 µl media)
    e) add 10 µl of every concentration to 60 µl media in the cell plate resulting in final concentration of DMSO: 0.3% in every well and resulting in 10 final concentration of compounds ranging from 30 µM to 0.0015 µM.
    Each compound is tested in triplicate.
    Incubate 120 h (5 days) at 37° C., 5% $CO_2$ Analysis:
  Add 30 µl CellTiter-Glo™ Reagent (containing luciferase, luciferan substrate, and buffer) per well,
  shake 15 minutes at room temperature
  incubate further 45 minutes at room temperature without shaking Measurement:
  Victor 2 scanning multiwell spectrophotometer (Wallac), Luminescence mode (0.5 sec/read, 477 nm)
  Determine IC50 using a non-linear curve fit (XLfit® software (ID Business Solution Ltd., Guilford, Surrey, UK))

With all compounds a significant inhibition of HCT 116 cell viability was detected, which is exemplified by the compounds shown in Table 1:

TABLE 1

Results:

| Examples | IC50 HCT 116 [µM] |
|---|---|
| 1-2 | 5.32 |
| 1-7 | 8.48 |
| 1-24 | 3.17 |
| 1-1, 1-3, 1-4, 1-8, 1-10, 1-13, 1-15, 1-18, 1-20, 1-21, 1-28, 1-29, 1-33, 1-38, 1-40, 1-45, 1-47, 1-49, 1-51, 1-54, 1-56, 1-59, 1-63, 1-68, 1-69, 1-71, 1-72, 1-78, 1-80 | 1.00-16.00 |

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically acceptable, inorganic or organic carriers. For example, lactose, corn starch or derivatives thereof, talc, stearic acids or it's salts and the like can be used as carriers for tablets, coated tablets, dragées and hard gelatine capsules. Suitable carriers for soft gelatine capsules are, for example, vegetable oils, waxes, fats, semi-solid and liquid polyols and the like. However, depending on the nature of the active substance carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical composition may, for example, comprise the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG (direct tabletting grade) | 125 | 105 | 30 | 150 |
| 3. | Sta-Rx 1500 (pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

The following examples and references are provided to aid the understanding of the present invention, the true scope of which is set forth in the appended claims. It is understood that modifications can be made in the procedures set forth without departing from the spirit of the invention.

Experimental Procedures:

General Procedure for the Preparation of Pyridine Sulfonic Acid Amides

6-Morpholin-4-yl-pyridine-3-sulfonic Acid Amide

6-Morpholin-4-yl-pyridine-3-sulfonyl chloride (1.25 g, 4.8 mmol) was dissolved in a 0.5M solution of ammonia in dioxane (20 mL) and the mixture stirred for 16 hours at room temperature. The mixture was filtered and concentrated in vacuo to afford 6-morpholin-4-yl-pyridine-3-sulfonic acid amide as a white solid 1.1 g (96% yield).

MS(ESI+): M=244 (M+H)

$^1$H-NMR (250 MHz, D$_6$-DMSO): 8.47 (1H, d, J 2), 7.85 (1H, dd, J 2, 9), 7.23 (2H, br s), 6.97 (1H, d, J 9), 3.71-3.67 (4H, m), 3.60-3.56 (4H, m).

General Procedure for the Preparation of Benzoyl Acid Chlorides 2,4-dichlorobenzoyl chloride 2,4-dichlorobenzoic acid (63 µL, 0.45 mmol) and N,N-dimethyl formamide (DMF) (50 µl) was dissolved in dichloromethane (10 mL). Oxalyl chloride (0.57 mL, 6.7 mmol) was added and the solution stirred at room temperature for 2 hours. The reaction was monitored to completion by LC-MS. The reaction was concentrated in vacuo to afford crude 2,4-dichlorobenzoyl chloride.

Final Products

Sodium Salt Formation

Depending on the work-up procedure i.e. the HPLC purification conditions, the final products described below (in Examples 1-1 to 1-82) were obtained either directly as sulfonamide sodium salts (neutral HPLC-conditions—e.g. aqueous eluent is water(pH is 7)/acetonitrile 9:1 and the organic eluent is acetonitrile) or they were obtained firstly as sulfonamide ammonium salts (basic HPLC conditions—e.g. with ammonium carbonate as buffer pH =10) or as sulfonamides in their salt free form acidic HPLC conditions (e.g. the aqueous eluent is water with 0.2% acetic acid and the organic eluent is acetonitrile with 0.2% acetic acid.

These obtained sulfonamides or sulfonamide ammonium salts are converted to their sodium salts using the following procedure:

To a solution of the sulfonamide or sulfonamide ammonium salt (1 eq., e.g. 1 mmol) in tetrahydrofuran (e.g. 10 mL), 1 eq. (e.g. 1 mmol) sodium methoxide (25% solution in methanol) is added and the mixture is stirred at room temperature for 1 hour. The tetrahydrofuran is removed in vacuo and the residue suspended in diethyl ether (e.g. 50 to 100 mL) and heated to reflux four 1 hour, cooled down to room temperature filtered off and dried.

EXAMPLE 1-1

6-morpholin-4-yl-pyridine-3-sulfonic acid 2,4-dichloro-benzoylamide; sodium salt Sodium hydride (60% dispersion in mineral oil) (34 mg, 0.9 mmol) was added to a solution of 6-morpholin-4-yl-pyridine-3-sulfonic acid (68 mg, 0.28 mmol) in dioxane (1 mL) and the mixture was shaken for 45 minutes. A solution of 2,4-dichlorobenzoyl chloride (61 µL, 0.42 mmol) in dioxane (0.5 mL) was added to the mixture and the whole shaken at room temperature for 2 hours. Water (0.2 mL) was added to the mixture and the whole was concentrated in vacuo. The resultant residue was purified by preparative HPLC under neutral conditions to give 6-morpholin-4-yl-pyridine-3-sulfonic acid 2,4-dichloro-benzoylamide as the sodium salt, 45.6 mg (37% yield).

MS (ESI+): M=416 (M+H)

$^1$H-NMR (500 MHz, $D_6$-DMSO): δ=8.31 (d, 1H, pyridine-2-H), 7.74 (m, 1H, pyridine-4-H), 7.27 (m, 2H, chlorophenyl-6-H, chlorophenyl-3-H), 7.14 (d, 1H, chlorophenyl-5-H), 6.62 (d, 1H pyridine-5-H), 3.52 (m, 4H, morpholine), 3.35 (m, 4H, morpholine).

The following examples were prepared in an analogous manner as described for example 1-1, using the appropriate starting material or they were prepared according to the schemes 1 or 2 above:

| Example No. | Systematic Name | MS (ESI+) | $^1$H-NMR(500MHz, $D_6$-DMSO) |
|---|---|---|---|
| 1-2 | 6-Morpholin-4-yl-pyridine-3-sulfonic acid 4-chloro-2-methyl-benzoylamide; sodium salt | 396.3 | 8.33(s, 1H, pyridine-2-H), 7.76(m, 1H, pyridine-4-H), 7.38(d, 1H, chlorophenyl-5-H), 6.98(m, 2H, chlorophenyl-3-H, chlorophenyl-6-H), 6.64(d, 1H pyridine-5-H), 3.45(m, 4H, morpholine), 3.36(m, 4H, morpholine), 2.19(s, 3H, methyl) |
| 1-3 | 6-Morpholin-4-yl-pyridine-3-sulfonic acid 4-bromo-2-methyl-benzoylamide; sodium salt | 440.2 | 8.45(s, 1H, pyridine-2-H), 7.86(m, 1H, pyridine-4-H), 7.43(m, 1H, bromophenyl-5-H), 7.23(m, 2H, bromophenyl-3-H, bromophenyl-6-H), 6.76(d, 1H pyridine-5-H), 3.66(m, 4H, morpholine), 3.48(m, 4H, morpholine), 2.30(s, 3H, methyl) |
| 1-4 | 6-Morpholin-4-yl-pyridine-3-sulfonic acid 2-bromo-4-methyl-benzoylamide; sodium salt | 440.2 | 8.48(s, 1H, pyridine-2-H), 7.91(d, 1H, pyridine-4-H), 7.31(m, 2H, bromophenyl-5-H, bromophenyl-3-H), 7.07(d, 1H, bromophenyl-6-H), 6.79(d, 1H pyridine-5-H), 3.66(m, 4H, morpholine), 3.51(m, 4H, morpholine), 2.25(s, 3H, methyl) |
| 1-5 | 5-Bromo-6-chloro-pyridine-3-sulfonic acid 2-bromo-4-methyl-benzoylamide; sodium salt | 467.1 | 8.67(s, 1H, pyridine-2-H), 8.42(s, 1H, pyridine-4-H), 7.31(m, 2H, bromophenyl-5-H, bromophenyl-3-H), 7.08(d, 1H, bromophenyl-6-H) |
| 1-6 | 5-Bromo-6-chloro-pyridine-3-sulfonic acid 2-bromo-4-fluoro-benzoylamide; sodium salt | 471.0 | 8.76(s, 1H, pyridine-2-H), 8.49(m, 1H, pyridine-4-H), 7.53(m, 1H, bromophenyl-6-H), 7.47(m, 1H, bromophenyl-3-H), 7.19(m, 1H, bromophenyl-5-H) |
| 1-7 | 5-Bromo-6-chloro-pyridine-3-sulfonic acid 4-bromo-2-chloro-benzoylamide; sodium salt | 487.0 | 8.69(s, 1H, pyridine-2-H), 8.42(m, 1H, pyridine-4-H), 7.56(s, 1H, chlorophenyl-3-H), 7.44(s, 1H, chlorophenyl-5-H), 7.40(d, 1H, chlorophenyl-6-H) |
| 1-8 | 5-Bromo-6-chloro-pyridine-3-sulfonic acid | 487.0 | 8.67(m, 1H, pyridine-2-H), 8.40(m, 1H, pyridine-4-H), 7.55(s, 1H, chlorophenyl-3-H), 7.40(s, |

| Example No. | Systematic Name | MS (ESI+) | ¹H-NMR(500MHz, D$_6$-DMSO) |
|---|---|---|---|
| | 2-bromo-4-chloro-benzoylamide; sodium salt | | 1H, chlorophenyl-5-H), 7.32(d, 1H, chlorophenyl-6-H) |
| 1-9 | 5-Bromo-6-chloro-pyridine-3-sulfonic acid 2,4-dimethyl-benzoylamide; sodium salt | 403.2 | 8.47(s, 1H, pyridine-2-H), 8.20(m, 1H, pyridine-4-H), 7.29(d, 1H, dimethylphenyl-5-H), 6.67(m, 2H, dimethylphenyl-3-H, dimethylphenyl-6-H), 2.09(s, 3H, methyl), 2.00(s, 3H, methyl) |
| 1-10 | 6-Morpholin-4-yl-pyridine-3-sulfonic acid 2-chloro-4-fluoro-benzoylamide; sodium salt | 400.3 | 8.43(d, 1H, pyridine-2-H), 7.86(m, 1H, pyridine-4-H), 7.46(t, 1H, fluorophenyl-6-H), 7.18(m, 1H, fluorophenyl-3-H), 7.03(m, 1H, fluorophenyl-5-H), 6.75(d, 1H pyridine-5-H), 3.64(m, 4H, morpholine), 3.47(m, 4H, morpholine) |
| 1-11 | 5-Bromo-6-chloro-pyridine-3-sulfonic acid 2-chloro-4-fluoro-benzoylamide; sodium salt | 427.1 | 8.51(s, 1H, pyridine-2-H), 8.24(m, 1H, pyridine-4-H), 7.36(t, 1H, chlorophenyl-6-H), 7.07(m, 1H, chlorophenyl-3-H), 6.92(m, 1H, chlorophenyl-5-H) |
| 1-12 | 6-Morpholin-4-yl-pyridine-3-sulfonic acid 4-chloro-2-fluoro-benzoylamide; sodium salt | 400.3 | 8.54(d, 1H, pyridine-2-H), 7.96(m, 1H, pyridine-4-H), 7.74(t, 1H, chlorophenyl-6-H), 7.32(d, 1H, chlorophenyl-5-H), 7.23(d, 1H, chlorophenyl-3-H), 6.85(d, 1H pyridine-5-H), 3.75(m, 4H, morpholine), 3.58(m, 4H, morpholine) |
| 1-13 | 5-Bromo-6-chloro-pyridine-3-sulfonic acid 2,4-dichloro-benzoylamide; sodium salt | 443.1 | 8.53(d, 1H, pyridine-2-H), 8.26(m, 1H, pyridine-4-H), 7.31(d, 1H, chlorophenyl-5-H), 7.27(s, 1H, chlorophenyl-3-H), 7.14(d, 1H, chlorophenyl-6-H) |
| 1-14 | 5-Bromo-6-chloro-pyridine-3-sulfonic acid 4-fluoro-2-trifluoromethyl-benzoylamide; sodium salt | 461.1 | 8.49(s, 1H, pyridine-2-H), 8.22(s, 1H, pyridine-4-H), 7.39(m, 1H, trifluoromethylphenyl-5-H), 7.23(m, 2H, trifluoromethylphenyl-3-H, trifluoromethylphenyl-6-H) |
| 1-15 | 6-Phenoxy-pyridine-3-sulfonic acid 2-fluoro-4-trifluoromethyl-benzoylamide; sodium salt | 441.3 | 8.50(d, 1H, pyridine-2-H), 8.19(m, 1H, pyridine-4-H), 7.82(t, 1H, fluorophenyl-6-H), 7.48(m, 4H, phenoxy-3-H, phenoxy-5-H, fluorophenyl-5-H, fluorophenyl-3-H), 7.26(t, 1H, phenoxy-4-H), 7.17(d, 2H, phenoxy-2-H, phenoxy-6-H), 7.03(d, 1H pyridine-5-H) |
| 1-16 | 6-Phenoxy-pyridine-3-sulfonic acid 4-bromo-2-fluoro-benzoylamide; sodium salt | 451.2 | 8.62(s, 1H, pyridine-2-H), 8.33(m, 1H, pyridine-4-H), 7.76(t, 1H, fluorophenyl-6-H), 7.57(t, 2H, phenoxy-3-H, phenoxy-5-H), 7.52(d, 1H, fluorophenyl-5-H), 7.466(d, 1H, fluorophenyl-3-H), 7.39(t, 1H, phenoxy-4-H), 7.31(d, 2H, phenoxy-2-H, phenoxy-6-H), 7.14(d, 1H pyridine-5-H) |
| 1-17 | 6-Morpholin-4-yl-pyridine-3-sulfonic acid 4-bromo-2-fluoro-benzoylamide; sodium salt | 444.2 | 8.39(d, 1H, pyridine-2-H), 7.76(m, 1H, pyridine-4-H), 7.45(m, 1H, fluorophenyl-6-H), 7.35(m, 1H, fluorophenyl-3-H), 7.28(d, 1H, fluorophenyl-5-H), 6.74(d, 1H pyridine-5-H), 3.50(m, 4H, morpholine), 3.44(m, 4H, morpholine) |
| 1-18 | 5-Bromo-6-chloro-pyridine-3-sulfonic acid 2,4-bis- | 511.1 | 8.66(s, 1H, pyridine-2-H), 8.39(d, 1H, pyridine-4-H), 7.92(d, 1H, trifluoromethylphenyl-6-H), 7.84(s, 1H, |

-continued

| Example No. | Systematic Name | MS (ESI+) | $^1$H-NMR(500MHz, D$_6$-DMSO) |
|---|---|---|---|
| | trifluoromethyl-benzoylamide; sodium salt | | trifluoromethylphenyl-3-H), 7.66(d, 1H, trifluoromethylphenyl-5-H) |
| 1-19 | 6-Phenoxy-pyridine-3-sulfonic acid 2-chloro-4-fluoro-benzoylamide; sodium salt | 407.2 | 8.27(d, 1H, pyridine-2-H), 7.98(m, 1H, pyridine-4-H), 7.33(t, 1H, fluorophenyl-6-H), 7.22(t, 2H, phenoxy-3-H, phenoxy-5-H), 7.03(m, 2H, fluorophenyl-3-H, phenoxy-4-H), 6.94(d, 2H, phenoxy-2-H, phenoxy-6-H), 6.88(m, 1H, fluorophenyl-5-H), 6.80(d, 1H pyridine-5-H) |
| 1-20 | 6-Phenoxy-pyridine-3-sulfonic acid 4-chloro-2-fluoro-benzoylamide; sodium salt | 407.2 | 8.38(s, 1H, pyridine-2-H), 8.10(m, 1H, pyridine-4-H), 7.59(t, 1H, fluorophenyl-6-H), 7.33(t, 2H, phenoxy-3-H, phenoxy-5-H), 7.15(m, 2H, fluorophenyl-5-H, phenoxy-4-H), 7.07(m, 3H, fluorophenyl-3-H, phenoxy-2-H, phenoxy-6-H), 6.91(d, 1H pyridine-5-H) |
| 1-21 | 6-Phenoxy-pyridine-3-sulfonic acid 4-fluoro-2-trifluoromethyl-benzoylamide; sodium salt | 441.2 | 8.24(d, 1H, pyridine-2-H), 7.94(m, 1H, pyridine-4-H), 7.34(m, 1H, trifluoromethylphenyl-6-H), 7.19(m, 4H, trifluoromethylphenyl-3-H, trifluoromethylphenyl-5-H, phenoxy-3-H, phenoxy-5-H), 7.00(t, 1H, phenoxy-4-H), 6.92(d, 2H, phenoxy-2-H, phenoxy-6-H), 6.79(d, 1H pyridine-5-H) |
| 1-22 | 6-Phenoxy-pyridine-3-sulfonic acid 2,4-bis-trifluoromethyl-benzoylamide; sodium salt | 491.3 | 8.42(d, 1H, pyridine-2-H), 8.11(m, 1H, pyridine-4-H), 7.88(d, 1H, trifluoromethylphenyl-6-H), 7.80(s, 1H, trifluoromethylphenyl-3-H), 7.61(d, 1H, trifluoromethylphenyl-5-H), 7.37(t, 2H, phenoxy-3-H, phenoxy-5-H), 7.17(t, 1H, phenoxy-4-H), 7.08(d, 2H, phenoxy-2-H, phenoxy-6-H), 6.97(d, 1H pyridine-5-H) |
| 1-23 | 6-Morpholin-4-yl-pyridine-3-sulfonic acid 2,4-bis-trifluoromethyl-benzoylamide; sodium salt | 484.3 | 8.32(d, 1H, pyridine-2-H), 8.78(m, 1H, pyridine-4-H), 7.74(d, 1H, trifluoromethylphenyl-6-H), 7.70(s, 1H, trifluoromethylphenyl-3-H), 7.49(d, 1H, trifluoromethylphenyl-5-H), 6.65(d, 1H pyridine-5-H), 3.53(m, 4H, morpholine), 3.38(m, 4H, morpholine) |
| 1-24 | Pyridine-3-sulfonic acid 2,4-dichloro-benzoylamide; sodium salt | 331.2 | 8.90(s, 1H, pyridine-2-H), 8.67(m, 1H, pyridine-4-H), 8.16(m, 1H, pyridine-6-H), 7.48(m, 2H, chlorophenyl-3-H, pyridine-5-H) 7.37(d, 1H, chlorophenyl-5-H), 7.29(d, 1H, chlorophenyl-6-H) |
| 1-25 | 6-Phenoxy-pyridine-3-sulfonic acid 4-chloro-2-methyl-benzoylamide; sodium salt | 403.3 | 8.25(d, 1H, pyridine-2-H), 7.96(m, 1H, pyridine-4-H), 7.33(d, 1H, chlorophenyl-5-H), 7.20(t, 2H, phenoxy-3-H, phenoxy-5-H), 7.00(t, 1H, phenoxy-4-H), 6.50(m, 4H, phenoxy-2-H, phenoxy-6-H, chlorophenyl-3-H, chlorophenyl-6-H), 6.77(d, 1H, pyridine-5-H) |
| 1-26 | 5-Bromo-6-chloro-pyridine-3-sulfonic acid 4-bromo-2-methyl-benzoylamide; sodium salt | 467.1 | 8.57(d, 1H, pyridine-2-H), 8.30(s, 1H, pyridine-4-H), 7.38(d, 1H, bromophenyl-5-H), 7.15(m, 2H, bromophenyl-3-H, bromophenyl-5-H) |

-continued

| Example No. | Systematic Name | MS (ESI+) | $^1$H-NMR(500MHz, D$_6$-DMSO) |
|---|---|---|---|
| 1-27 | 6-Phenoxy-pyridine-3-sulfonic acid 2-bromo-4-fluoro-benzoylamide; sodium salt | 451.1 | 8.28(d, 1H, pyridine-2-H), 8.00(m, 1H, pyridine-4-H), 7.29(t, 1H, fluorophenyl-6-H), 7.21(m, 3H, phenoxy-3-H, phenoxy-5-H, fluorophenyl-3-H), 7.03(t, 1H, phenoxy-4-H), 6.95(m, 3H, phenoxy-2-H, phenoxy-6-H, fluorophenyl-5-H), 6.82(d, 1H, pyridine-5-H) |
| 1-28 | 6-Phenoxy-pyridine-3-sulfonic acid 4-bromo-2-chloro-benzoylamide; sodium salt | 467.0 | 8.49(d, 1H, pyridine-2-H), 8.20(m, 1H, pyridine-4-H), 7.56(s, 1H, chlorophenyl-3-H), 7.42(m, 4H, phenoxy-3-H, phenoxy-5-H, chlorophenyl-5-H, chlorophenyl-6-H), 7.26(t, 1H, phenoxy-4-H), 7.17(d, 2H, phenoxy-2-H, phenoxy-6-H), 7.02(d, 1H, pyridine-5-H) |
| 1-29 | 6-Morpholin-4-yl-pyridine-3-sulfonic acid 2-bromo-4-chloro-benzoylamide; sodium salt | 460.2 | 8.29(d, 1H, pyridine-2-H), 7.72(m, 1H, pyridine-4-H), 7.37(s, 1H, chlorophenyl-3-H), 7.22(s, 1H, chlorophenyl-5-H), 7.49(d, 1H, chlorophenyl-6-H), 6.60(d, 1H, pyridine-5-H), 3.50(m, 4H, morpholine), 3.32(m, 4H, morpholine) |
| 1-30 | 5-Bromo-6-chloro-pyridine-3-sulfonic acid 4-chloro-2-methyl-benzoylamide; sodium salt | 423.1 | 8.49(d, 1H, pyridine-2-H), 8.22(m, 1H, pyridine-4-H), 7.36(d, 1H, chlorophenyl-5-H), 6.94(m, 2H, chlorophenyl-5-H, chlorophenyl-6-H) |
| 1-31 | 5-Bromo-6-chloro-pyridine-3-sulfonic acid 2-fluoro-4-trifluoromethyl-benzoylamide; sodium salt | 461.1 | 8.52(s, 1H, pyridine-2-H), 8.25(s, 1H, pyridine-4-H), 7.63(m, 1H, fluorophenyl-6-H), 7.34(d, 1H, fluorophenyl-3-H), 7.29(d, 1H, fluorophenyl-5-H) |
| 1-32 | 5-Bromo-6-chloro-pyridine-3-sulfonic acid 4-bromo-2-fluoro-benzoylamide; sodium salt | 471.0 | 8.61(s, 1H, pyridine-2-H), 8.34(s, 1H, pyridine-4-H), 7.54(m, 1H, bromophenyl-6-H), 7.31(m, 1H, bromophenyl-3-H), 7.23(d, 1H, bromophenyl-5-H) |
| 1-33 | 6-Phenoxy-pyridine-3-sulfonic acid 2-bromo-4-chloro-benzoylamide; sodium salt | 467.2 | 8.34(d, 1H, pyridine-2-H), 8.05(m, 1H, pyridine-4-H), 7.43(s, 1H, chlorophenyl-3-H), 7.29(m, 3H, phenoxy-3-H, phenoxy-5-H, chlorophenyl-5-H), 7.22(m, 1H, chlorophenyl-6-H), 7.09(t, 1H, phenoxy-4-H), 7.01(d, 2H, phenoxy-2-H, phenoxy-6-H), 6.87(d, 1H, pyridine-5-H) |
| 1-34 | 6-Phenoxy-pyridine-3-sulfonic acid 2,4-dichloro-benzoylamide; sodium salt | 423.2 | 8.39(s, 1H, pyridine-2-H), 8.10(m, 1H, pyridine-4-H), 7.36(m, 4H, phenyl-3-H, phenyl-6-H, phenoxy-3-H, phenoxy-5-H), 7.22(d, 1H, phenyl-5-H), 7.14(t, 1H, phenoxy-4-H), 7.07(d, 2H, phenoxy-2-H, phenoxy-6-H), 6.92(d, 1H, pyridine-5-H), |
| 1-35 | 6-Morpholin-4-yl-pyridine-3-sulfonic acid 4-fluoro-2-trifluoromethyl-benzoylamide; sodium salt | 434.3 | 8.36(s, 1H, pyridine-2-H), 7.79(m, 1H, pyridine-4-H), 7.44(m, 1H, phenyl-6-H), 7.31(m, 2H, phenyl-3-H, phenyl-5-H), 6.69(d, 1H pyridine-5-H), 3.59(m, 4H, morpholine), 3.42(m, 4H, morpholine) |
| 1-36 | 6-Morpholin-4-yl-pyridine-3-sulfonic acid 2-fluoro-4- | 434.3 | 8.25(s, 1H, pyridine-2-H), 7.67(m, 1H, pyridine-4-H), 7.54(m, 1H, phenyl-6-H), 7.26(m, 2H, phenyl-3-H, phenyl-5-H), |

-continued

| Example No. | Systematic Name | MS (ESI+) | ¹H-NMR(500MHz, D₆-DMSO) |
|---|---|---|---|
| | trifluoromethyl-benzoylamide; sodium salt | | 6.56(d, 1H pyridine-5-H), 3.45(m, 4H, morpholine), 3.28(m, 4H, morpholine) |
| 1-37 | Pyridine-3-sulfonic acid 4-fluoro-2-trifluoromethyl-benzoylamide; sodium salt | 349.3 | 8.91(s, 1H, pyridine-2-H), 8.60(d, 1H, pyridine-4-H), 8.13(d, 1H, pyridine-6-H), 7.57(m, 1H, phenyl-6-H), 7.66(m, 3H, phenyl-3-H, phenyl-5-H, pyridine-5-H) |
| 1-38 | Pyridine-3-sulfonic acid 2,4-bis-trifluoromethyl-benzoylamide; sodium salt | 399.2 | 8.71(s, 1H, pyridine-2-H), 8.41(d, 1H, pyridine-4-H), 7.93(d, 1H, pyridine-6-H), 7.75(d, 1H, phenyl-6-H), 7.66(s, 1H, phenyl-3-H), 7.48(d, 1H, phenyl-5-H), 7.26(m, 1H pyridine-5-H) |
| 1-39 | 6-Phenoxy-pyridine-3-sulfonic acid 4-bromo-2-methyl-benzoylamide; sodium salt | 447.2 | 8.27(s, 1H, pyridine-2-H), 7.98(m, 1H, pyridine-4-H), 7.28(d, 1H, phenyl-6-H), 7.22(t, 2H, phenoxy-3-H, phenoxy-5-H), 7.04(m, H, phenyl-3-H, phenyl-5-H, phenoxy-4-H), 6.94(d, 2H, phenoxy-2-H, phenoxy-6-H), 6.79(d, 1H, pyridine-5-H), 2.11(s, 3H, methyl) |
| 1-40 | 6-Phenoxy-pyridine-3-sulfonic acid 2-bromo-4-methyl-benzoylamide; sodium salt | 447.2 | 8.49(s, 1H, pyridine-2-H), 8.19(m, 1H, pyridine-4-H), 7.44(t, 2H, phenoxy-3-H, phenoxy-5-H), 7.35(d, 1H, phenyl-5-H), 7.30(s, 1H, phenyl-3-H), 7.24(t, 1H, phenoxy-4-H), 7.15(d, 2H, phenoxy-2-H, phenoxy-6-H), 7.09(d, 1H, phenyl-6-H), 7.01(d, 1H, pyridine-5-H), 2.26(s, 3H, methyl) |
| 1-41 | 6-Morpholin-4-yl-pyridine-3-sulfonic acid 2-bromo-4-fluoro-benzoylamide; sodium salt | 444.2 | 8.32(s, 1H, pyridine-2-H), 7.73(m, 1H, pyridine-4-H), 7.31(m, 1H, phenyl-3-H), 7.22(m, 1H, phenyl-6-H), 6.96(m, 1H, phenyl-5-H), 6.63(d, 1H pyridine-5-H), 3.52(m, 4H, morpholine), 3.35(m, 4H, morpholine) |
| 1-42 | 6-Phenoxy-pyridine-3-sulfonic acid 2,4-dimethyl-benzoylamide; sodium salt | 383.3 | 8.26(s, 1H, pyridine-2-H), 7.97(m, 1H, pyridine-4-H), 7.27(d, 1H, phenyl-6-H), 7.22(t, 2H, phenoxy-3-H, phenoxy-5-H), 7.03(t, 1H, phenoxy-4-H), 6.93(d, 2H, phenoxy-2-H, phenoxy-6-H), 6.78(d, 1H, phenyl-5-H), 6.67(m, 2H, phenyl-3-H, pyridine-5-H), 2.10(s, 3H, methyl), 2 01(s, 3H, methyl) |
| 1-43 | 6-Morpholin-4-yl-pyridine-3-sulfonic acid 2,4-dimethyl-benzoylamide; sodium salt | 376.4 | 8.49(s, 1H, pyridine-2-H), 7.92(m, 1H, pyridine-4-H), 7.47(d, 1H, phenyl-6-H), 6.88(m, 2H, phenyl-3-H, phenyl-5-H), 6.79(d, 1H pyridine-5-H), 3.70(m, 4H, morpholine), 3.51(m, 4H, morpholine), 2.32(s, 3H, methyl), 2.23(s, 3H, methyl) |
| 1-44 | Pyridine-3-sulfonic acid 2-bromo-4-fluoro-benzoylamide; sodium salt | 359.2 | 8.97(s, 1H, pyridine-2-H), 8.64(d, 1H, pyridine-4-H), 8.19(d, 1H, pyridine-6-H), 7.54(t, 1H, phenyl-5-H), 7.49(m, 1H, phenyl-6-H), 7.43(m, 1H, phenyl-3-H), 7.19(m, 1H pyridine-5-H) |
| 1-45 | 4-Methoxy-3,4,5,6-tetrahydro-2H-[1,2']bipyridinyl-5'-sulfonic acid 4-chloro-2-methoxy-benzoylamide; sodium salt | | 1.46(m, 2H), 1.90(m, 2H), 3.28(s, 3H), 3.40(m, 2H), 3.48(m, 1H), 3.85(s, 3H), 4.02(m, 2H), 6.96(d, 1H), 7.05(d, 1H), 7.21(s, 1H), 7.42(d, 1H), 7.90(d, 1H), 8.56(d, 1H) |

-continued

| Example No. | Systematic Name | MS (ESI+) | $^1$H-NMR(500MHz, D$_6$-DMSO) |
|---|---|---|---|
| 1-46 | 4-Methoxy-3,4,5,6-tetrahydro-2H-[1,2']bipyridinyl-5'-sulfonic acid 2,4-dichloro-benzoylamide | | 1.46(m, 2H), 1.90(m, 2H), 3.28(s, 3H), 3.41(m, 2H), 3.50(m, 1H), 4.03(d, 2H), 6.98(d, 1H), 7.49(m, 2H), 7.68(s, 1H), 7.90(d, 1H), 8.57(s, 1H) |
| 1-47 | 6-Thiomorpholin-4-yl-pyridine-3-sulfonic acid 4-chloro-2-methoxy-benzoylamide | | 2.65(m, 4H), 3.86(s, 3H), 4.03(m, 4H), 6.98(d, 1H), 7.06(d, 1H), 7.21(s, 1H), 7.43(d, 1H), 7.93(d, 1H), 8.58(s, 1H) |
| 1-48 | 4-Methyl-3,4,5,6-tetrahydro-2H-[1,2']bipyridinyl-5'-sulfonic acid 4-chloro-2-trifluoromethyl-benzoylamide | | 0.94(d, 3H), 1.09(m, 2H), 1.25(m, 1H), 1.72(m, 2H), 2.97(m, 2H), 4.44(d, 2H), 6.93(d, 1H), 7.61(d, 1H), 7.81(d, 1H), 7.87(m, 2H), 8.54(s, 1H), |
| 1-49 | 6-Azepan-1-yl pyridine-3-sulfonic acid 4-chloro-2-trifluoromethyl-benzoylamide | | 1.49(m, 4H), 1.74(m, 4H), 3.70(m, 4H?), 6.74(d, 1H), 7.60(d, 1H), 7.79(d, 1H), 7.84(s, 1H), 7.87(d, 1H), 8.53(s, 1H) |
| 1-50 | 6-Pyrrolidin-1-yl-pyridine-3-sulfonic acid 4-chloro-2-trifluoromethyl-benzoylamide; ammonium salt | | 1.96(m, 4H), 3.44(m, 4H), 6.44(d, 1H), 7.51(d, 1H), 7.66(m, 2H), 7.84(d, 1H), 8.45(s, 1H) |
| 1-51 | 3-Methyl-3,4,5,6-tetrahydro-2H-[1,2']bipyridinyl-5'-sulfonic acid 4-chloro-2-trifluoromethyl-benzoylamide; ammonium salt | | 0.76(d, 3H), 1.23(m, 1H), 1.47(m, 1H), 1.59(m, 1H), 1.72(m, 1H), 1.82(m, 1H), 2.68(t, 1H), 2.98(t, 1H), 4.32(d, 2H), 6.93(d, 1H), 7.60(d, 1H), 7.80(d, 1H), 7.86(d, 2H), 8.53(d, 1H) |
| 1-52 | 4-Methoxy-3,4,5,6-tetrahydro-2H-[1,2']bipyridinyl-5'-sulfonic acid 4-chloro-2-trifluoromethyl-benzoylamide; ammonium salt | | 1.46(m, 2H), 1.90(m, 2H), 3.28(s, 3H), 3.39(m, 2H), 3.49(m, 1H), 4.03(m, 2H), 6.95(d, 1H), 7.60(d, 1H), 7.79(d, 1H), 7.84(s, 1H), 7.89(d, 1H), 8.54(d, 1H) |
| 1-53 | 6-(2,6-Dimethyl-morpholin-4-yl)-pyridine-3-sulfonic acid 4-chloro-2-trifluoromethyl-benzoylamide | | 1.18(d, 6H), 2.59(m, 2H), 3.60(m, 2H), 4.34(d, 2H), 6.97(d, 1H), 7.60(d, 1H), 7.80(d, 1H), 7.86(s, 1H), 7.93(d, 1H), 8.57(d, 1H), |
| 1-54 | 6-Dipropylamino-pyridine-3-sulfonic acid 4-chloro-2-trifluoromethyl-benzoylamide | | 0.90(t, 6H), 1.59(m, 4H), 3.50(t, 4H), 6.75(d, 1H), 7.62(d, 1H), 7.82(d, 1H), 7.86(m, 2H), 8.53(d, 1H) |
| 1-55 | 6-(Hexyl-methyl-amino)-pyridine-3-sulfonic acid 4-chloro-2-trifluoromethyl-benzoylamide; ammonium salt | | 0.87(t, 3H), 1.29(m, 6H), 1.56(m, 2H), 3.10(s, 3H), 3.60(t, 2H), 6.75(d, 1H), 7.61(d, 1H), 7.82(d, 1H), 7.88(m, 2H), 8.55(d, 1H) |

-continued

| Example No. | Systematic Name | MS (ESI+) | ¹H-NMR(500MHz, D₆-DMSO) |
|---|---|---|---|
| 1-56 | 6-Thiomorpholin-4-yl-pyridine-3-sulfonic acid 4-chloro-2-trifluoromethyl-benzoylamide; ammonium salt | | 2.66(m, 4H), 4.05(m, 4H), 6.99(d, 1H), 7.63(d, 1H), 7.82(d, 1H), 7.88(s, 1H), 7.94(d, 1H), 8.59(d, 1H) |
| 1-57 | 6-(Ethyl-methyl-amino)-pyridine-3-sulfonic acid 4-chloro-2-trifluoromethyl-benzoylamide; ammonium salt | | 1.12(t, 3H), 3.10(s, 3H), 3.65(q, 2H), 6.77(d, 1H), 7.61(d, 1H), 7.83(d, 1H), 7.89(m, 2H), 8.56(d, 1H) |
| 1-58 | 6-(Methyl-propyl-amino)-pyridine-3-sulfonic acid 4-chloro-2-trifluoromethyl-benzoylamide; ammonium salt | | 0.88(t, 3H), 1.59(m, 2H), 3.11(s, 3H), 3.57(t, 2H), 6.77(d, 1H), 7.61(d, 1H), 7.82(d, 1H), 7.88(m, 2H), 8.55(d, 1H) |
| 1-59 | 6-(Butyl-ethyl-amino)-pyridine-3-sulfonic acid 4-chloro-2-trifluoromethyl-benzoylamide; ammonium salt | | 0.93(t, 3H), 1.14(t, 3H), 1.33(m, 2H), 1.56(m, 2H), 3.53(m, 2H), 3.58(m, 2H), 6.73(d, 1H), 7.62(d, 1H), 7.82(d, 1H), 7.87(m, 2H), 8.54(d, 1H) |
| 1-60 | 6-Pyrrolidin-1-yl-pyridine-3-sulfonic acid 4-chloro-2-methoxy-benzoylamide; ammonium salt | | |
| 1-61 | 4-Methyl-3,4,5,6-tetrahydro-2H-[1,2']bipyridinyl-5'-sulfonic acid 2,4-dichloro-benzoylamide; ammonium salt | | 0.93(d, 3H), 1.09(m, 2H), 1.73(m, 3H), 2.97(m, 2H), 4.43(d, 2H), 6.94(d, 1H), 7.49(m, 2H), 7.68(s, 1H), 7.89(d, 1H), 8.56(d, 1H) |
| 1-62 | 4-Methyl-3,4,5,6-tetrahydro-2H-[1,2']bipyridinyl-5'-sulfonic acid 2-chloro-4-fluoro-benzoylamide | | 2.65(d, 3H), 2.80(m, 1H), 3.43(m, 4H), 4.68(t, 2H), 6.16(m, 2H), 8.67(d, 1H), 9.00(m, 1H), 9.23(d, 1H), 9.28(m, 1H), 9.61(dd, 1H), 10.28(m, 1H), |
| 1-63 | 6-(Methyl-propyl-amino)-pyridine-3-sulfonic acid 2-chloro-4-fluoro-benzoylamide | | 0.89(m, 3H), 1.57(m, 2H), 3.11(s, 3H), 3.57(m, 2H), 6.76(d, 1H), 7.28(m, 1H), 7.51(d, 1H), 7.55(m, 1H), 7.90(dd, 1H), 8.57(m, 1H), |
| 1-64 | 6-Azepan-1-yl-pyridine-3-sulfonic acid 4-chloro-2-methoxy-benzoylamide | | 1.50(m, 4H), 1.73(m, 4H), 3.69(m, 4H), 3.85(s, 3H), 6.77(d, 1H), 7.06(d, 1H), 7.22(s, 1H), 7.43(d, 1H), 7.89(dd, 1H), 8.55(d, 1H), |
| 1-65 | 6-Azepan-1-yl-pyridine-3-sulfonic acid 2-chloro-4-fluoro-benzoylamide | | 1.50(m, 4H), 1.74(m, 4H), 3.70(m, 4H), 6.78(d, 1H), 7.28(m, 1H), 7.51(d, 1H), 7.56(m, 1H), 7.89(dd, 1H), 8.56(m, 1H), |
| 1-66 | 6-Pyrrolidin-1-yl-pyridine-3-sulfonic acid 2-chloro-4-fluoro-benzoylamide | | 1.97(m, 4H), 4H under solvent, 6.59(d, 1H), 7.28(m, 1H), 7.54(m, 2H), 7.91(dd, 1H), 8.58(m, 1H), |

-continued

| Example No. | Systematic Name | MS (ESI+) | ¹H-NMR(500MHz, D$_6$-DMSO) |
|---|---|---|---|
| 1-67 | 3-Methyl-3,4,5,6-tetrahydro-2H-[1,2']bipyridinyl-5'-sulfonic acid 2-chloro-4-fluoro-benzoylamide | | 0.92(d, 3H), 1.22(m, 1H), 1.44(m, 1H), 1.58(m, 1H), 1.72(m, 1H), 1.81(m, 1H), 2.68(t, 1H), 2.98(t, 1H), 4.33(m, 2H), 6.96(d, 1H), 7.28(m, 1H), 7.51(d, 1H), 7.56(m, 1H), 7.89(dd, 1H), 8.56(m, 1H) |
| 1-68 | 6-Thiomorpholin-4-yl-pyridine-3-sulfonic acid 2-chloro-4-fluoro-benzoylamide | | 1.65(m, 4H), 4.05(m, 4H), 6.99(d, 1H), 7.28(m, 1H), 7.52(d, 1H), 7.57(m, 1H), 7.94(dd, 1H), 8.60(m, 1H), |
| 1-69 | 6-Azepan-1-yl-pyridine-3-sulfonic acid 2,4-dichloro-benzoylamide | | 1.49(m, 4H), 1.74(m, 4H), 2H under solvent, 3.70(m, 2H), 6.78(d, 1H), 7.50(m, 2H), 7.69(s, 1H), 7.89(dd, 1H), 8.56(m, 1H), |
| 1-70 | 6-Pyrrolidin-1-yl-pyridine-3-sulfonic acid 2,4-dichloro benzoylamide | | 1.98(m, 4H), 4H under solvent, 6.59(d, 1H), 7.49(m, 2H), 7.69(s, 1H), 7.90(dd, 1H), 8.58(m, 1H), |
| 1-71 | 6-Thiomorpholin-4-yl-pyridine-3-sulfonic acid 2,4-dichloro-benzoylamide | | 2.65(m, 4H), 4.04(m, 4H), 6.99(d, 1H), 7.50(m, 2H), 7.69(s, 1H), 7.94(dd, 1H), 8.59(m, 1H), |
| 1-72 | 6-((2R,6S)-2,6-Dimethyl-morpholin-4-yl)-pyridine-3-sulfonic acid 4-chloro-2-trifluoromethyl-benzoylamide | | 1.17(d, 6H), 2H under solvent, 3.59(m, 2H), 4.35(m, 2H), 6.99(d, 1H), 7.62(d, 1H), 7.83(d, 1H), 7.89(s, 1H), 7.94(dd, 1H), 8.58(m, 1H), |
| 1-73 | 3-Methyl-3,4,5,6-tetrahydro-2H-[1,2']bipyridinyl-5'-sulfonic acid 2,4-dichloro-benzoylamide | | 0.92(d, 3H), 1.25(m, 2H), 1.57(m, 1H), 1.71(m, 1H), 1.80(m, 1H), 2.68(t, 1H), 2.98(t, 1H), 4.33(m, 2H), 6.96(d, 1H), 7.50(m, 2H), 7.69(s, 1H), 7.89(dd, 1H), 8.55(m, 1H), |
| 1-74 | 6-(2,6-Dimethyl-morpholin-4-yl)-pyridine-3-sulfonic acid 2,4-dichloro-benzoylamide | | 1.16(m, 6H), 3.59(m, 2H), 3.81(m, 1H), 4.03(m, 1H), 4.35(m, 2H), 6.99(d, 1H), 7.50(m, 2H), 7.69(s, 1H), 7.94(d, 1H), 8.59(m, 1H), |
| 1-75 | 6-(Methyl-propyl-amino)-pyridine-3-sulfonic acid 2,4-dichloro-benzoylamide | | 0.88(t, 3H), 1.58(m, 2H), 3.10(s, 3H), 3.56(m, 2H), 6.76(d, 1H), 7.49(m, 2H), 7.68(s, 1H), 7.89(dd, 1H), 8.56(m, 1H), |
| 1-76 | 6-((2S,6R)-2,6-Dimethyl-morpholin-4-yl)-pyridine-3-sulfonic acid 2,4-dichloro-benzoylamide | | 1.17(d, 6H), 2H under solvent, 3.59(m, 2H), 4.34(m, 2H), 6.99(d, 1H), 7.49(m, 2H), 7.68(s, 1H), 7.94(dd, 1H), 8.59(m, 1H), |
| 1-77 | 4-Methyl-3,4,5,6-tetrahydro-2H-[1,2']bipyridinyl-5'-sulfonic acid 4-fluoro-2-trifluoromethyl-benzoylamide | | 0.93(d, 3H), 1.07(m, 2H), 1.47(m, 1H), 1.71(m, 2H), 2.97(t, 2H), 4.44(m, 2H), 6.95(d, 1H), 7.60(m, 1H), 7.67(m, 1H), 7.72(m, 1H), 7.87(dd, 1H), 8.55(m, 1H), |
| 1-78 | 6-Azepan-1-yl-pyridine-3-sulfonic acid 4-fluoro-2- | | 1.49(m, 4H), 1.74(m, 4H), 2H under solvent, 3.71(m, 2H), 6.78(d, 1H), 7.60(m, 1H), 7.69(m, 2H), 7.88(dd, 1H), 8.55(m, |

-continued

| Example No. | Systematic Name | MS (ESI+) | $^1$H-NMR(500MHz, D$_6$-DMSO) |
|---|---|---|---|
| | trifluoromethyl-benzoylamide | | 1H), |
| 1-79 | 6-Pyrrolidin-1-yl-pyridine-3-sulfonic acid 4-fluoro-2-trifluoromethyl-benzoylamide | | 1.98(m, 4H), 4H under solvent, 6.60(d, 1H), 7.61(m, 1H), 7.66(m, 1H), 7.73(d, 1H), 7.89(dd, 1H), 8.57(m, 1H), |
| 1-80 | 6-Thiomorpholin-4-yl-pyridine-3-sulfonic acid 4-fluoro-2-trifluoromethyl-benzoylamide | | 2.65(m, 4H), 4.05(m, 4H), 6.99(d, 1H), 7.61(m, 1H), 7.68(m, 1H), 7.73(m, 1H), 7.93(dd, 1H), 8.59(m, 1H), |
| 1-81 | 6-(Butyl-ethyl-amino)-pyridine-3-sulfonic acid 4-fluoro-2-trifluoromethyl-benzoylamide | | 0.93(t, 3H), 1.13(t, 3H), 1.33(m, 2H), 1.55(m, 2H), 3.52(m, 2H), 3.58(m, 2H), 6.73(d, 1H), 7.60(m, 1H), 7.69(m, 2H), 7.87(dd, 1H), 8.54(m, 1H), |
| 1-82 | 4-Methyl-3,4,5,6-tetrahydro-2H-[1,2']bipyridinyl-5'-sulfonic acid 4-chloro-2-methoxy-benzoylamide | | 0.93(d, 3H), 1.08(m, 2H), 1.71(m, 3H), 2.95(t, 2H), 3.86(s, 3H), 4.44(m, 2H), 6.94(d, 1H), 7.06(d, 1H), 7.22(s, 1H), 7.42(d, 1H), 7.88(dd, 1H), 8.55(m, 1H), |

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound according to formula Ia,

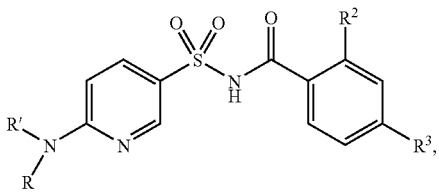

formula Ia wherein:
R and R', together with the nitrogen atom to which they are attached, form a heterocycle optionally substituted one to three times by alkyl or alkoxy, said heterocycle being selected from the group consisting of: pyrrolidine, morpholine, thiomorpholine, piperidine, and azepane;

$R^2$ is selected from the group consisting of: fluorine, chlorine, bromine, methyl, methoxy, and trifluoromethyl; and $R^3$ is selected from the group consisting of: fluorine, chlorine, bromine, menthyl, and trifluoromethyl;

or a pharmaceutically-acceptable salt thereof.

2. A pharmaceutical composition comprising a compound of claim 1 and a pharmaceutically acceptable carrier.

3. A compound according to claim 1 selected from the group consisting of:
a sodium salt of 6-morpholin-4-yl-pyridine-3-sulfonic acid 2,4-dichloro-benzoylamide;
a sodium salt of 6-morpholin-4-yl-pyridine-3-sulfonic acid 4-chloro-2-methyl-benzoylamide;
a sodium salt of 6-morpholin-4-yl-pyridine-3-sulfonic acid 4-bromo-2-methyl-benzoylamide;
a sodium salt of 6-morpholin-4-yl-pyridine-3-sulfonic acid 2-bromo-4-methyl-benzoylamide;
a sodium salt of 6-morpholin-4-yl-pyridine-3-sulfonic acid 2-chloro-4-fluoro-benzoylamide;
a sodium salt of 6-morpholin-4-yl-pyridine-3-sulfonic acid 4-chloro-2-fluoro-benzoylamide;
a sodium salt of 6-morpholin-4-yl-pyridine-3-sulfonic acid 4-bromo-2-fluoro-benzoylamide; a
sodium salt of 6-morpholin-4-yl-pyridine-3-sulfonic acid 2,4-bis-trifluoromethyl-benzoylamide;
a sodium salt of 6-morpholin-4-yl-pyridine-3-sulfonic acid 2,4-bis-trifluoromethyl-benzoylamide;
a sodium salt of 6-morpholin-4-yl-pyridine-3-sulfonic acid 4-fluoro-2-trifluoromethyl-benzoylamide;
a sodium salt of 6-morpholin-4-yl-pyridine-3-sulfonic acid 2-fluoro-4-trifluoromethyl-benzoylamide;
a sodium salt of 6-morpholin-4-yl-pyridine-3-sulfonic acid 2-bromo-4-fluoro-benzoylamide;
a sodium salt of 6-morpholin-4-yl-pyridine-3-sulfonic acid 2,4-dimethyl-benzoylamide;
a sodium salt of 4-methoxy-3,4,5,6-tetrahydro-2H-[1,2']bipyridinyl-5'-sulfonic acid 4-chloro-2-methoxy-benzoylamide;
4-methoxy-3,4,5,6-tetrahydro-2H-[1,2']bipyridinyl-5'-sulfonic acid 2,4-dichioro-benzoylamide;
6-thiomorpholin-4-yl-pyridine-3-sulfonic acid 4-chloro-2-methoxy-benzoylamide;

4-methyl-3,4,5,6-tetrahydro-2H-[1,2']bipyridinyl-5'-sulfonic acid 4-chloro-2-trifluoromethyl-benzoylamide;
6-azepan-1-yl-pyridine-3-sulfonic acid 4-chloro-2-trifluoromethyl-benzoylamide;
6-pyrrolidin-1-yl-pyridine-3-sulfonic acid 4-chloro-2-trifluoromethyl-benzoylamide; an ammonium salt of 3-methyl-3,4,5,6-tetrahydro-2H-[1,2']bipyridinyl-5'-sulfonic acid 4-chloro-2-methoxy-benzoylamide; an ammonium salt of
4-methoxy-3,4,5,6-tetrahydro-2H-[1,2']bipyridinyl-5'-sulfonic acid 4-chloro-2-trifluoromethyl-benzoylamide; an ammonium salt of
6-(2,6-dimethyl-morpholin-4-yl)-pyridine-3-sulfonic acid 4-chloro-2-trifluoromethyl-benzoylamide;
6-thiomorpholin-4-yl-pyridine-3-sulfonic acid 4-chloro-2-trifluoromethyl-benzoylamide; an ammonium salt of
6-pyrrolidin-1-yl-pyridine-3-sulfonic acid 4-chloro-2-methoxy-benzoylamide; an ammonium salt of
4-methyl-3,4,5,6-tetrahydro-2H-[1,2']bipyridinyl-5'-sulfonic acid 2,4-dichloro-benzoylamide; an ammonium salt of
4-methyl-3,4,5,6-tetrahydro-2H-[1,2']bipyridinyl-5'-sulfonic acid 2-chloro-4-fluoro-benzoylamide;
6-azepan-1-yl-pyridine-3-sulfonic acid 4-chloro-2-methoxy-benzoylamide;
6-azepan-1-yl-pyridine-3-sulfonic acid 2-chloro-4-fluoro-benzoylamide;
6-pyrrolidin-1-yl-pyridine-3-sulfonic acid 2-chloro-4-fluoro-benzoylamide;
3-methyl-3,4,5,6-tetrahydro-2H-[1,2∝]bipyridinyl-5'-sulfonic acid 2-chloro-4-fluoro-benzoylamide;
6-thiomorphin-4-yl-pyridine-3-sulfonic acid 2-chloro-4-fluoro-benzoylamide;
6-azepan-1-yl-pyridine-3-sulfonic acid 2,4-dichloro-benzoylamide;
6-pyrrolidin-1-yl-pyridine-3-sulfonic acid 2,4-dichloro-benzoylamide;
6-thiomorpholin-4-yl-pyridine-3-sulfonic acid 2,4-dichloro-benzoylamide;
6-((2R,6S)-2,6-dimethyl-morpholin-4-yl)-pyridine-3-sulfonic acid 4-chloro-2-trifluoromethyl-benzoylamide;
3-methyl-3,4,5,6-tetrahydro-2H-[1,2']bipyridinyl-5'-sulfonic acid 2,4-dichioro-benzoylamide;
6-(2,6-dimethyl-morpholin-4-yl)-pyridine-3-sulfonic acid 2,4-dichloro-benzoylamide;
6-((2R,6S)-2,6-dimethyl-morpholin-4-yl)-pyridine-3-sulfonic acid 2,4-dichioro-benzoylamide;
4-methyl-3,4,5,6-tetrahydro-2H-[1,2']bipyridinyl-5'-sulfonic acid 4-fluoro-2-trifluoromethyl-benzoylamide;
6-azepan-1-yl-pyridine-3-sulfonic acid 4-fluoro-2-trifluoromethyl-benzoylamide;
6-pyrrolidin-1-yl-pyridine-3-sulfonic acid 4-fluoro-2-trifluoromethyl-benzoylamide;
6-thiomorphin-4-yl-pyridine-3-sulfonic acid 4-fluoro-2-trifluoromethyl-benzoylamide; and
4-methyl-3,4,5,6-tetrahydro-2H-[1,2']bipyridinyl-5'-sulfonic acid 4-chloro-2-methoxy-benzoylamide.

4. A compound according to claim 1, wherein said heterocycle is optionally substituted once or twice by alkyl or alkoxy.

5. A compound according to claim 1, wherein $R^2$ is selected from the group consisting of: chlorine, bromine, methyl, methoxy, and trifluoromethyl.

6. A compound according to claim 4 wherein $R^2$ is selected from the group consisting of: chlorine, bromine, methyl, methoxy, and trifuoromethy.

7. A compound according to claim 5 wherein:
$R^2$ is selected from the group consisting of: chlorine and trifluoromethyl; and
$R^3$ is selected from the group consisting of: fluorine and chlorine.

8. A compound according to claim 7 selected from the group consisting of:
6-morpholin-4-yl-pyridine-3-sulfonic acid 2,4-dichloro-benzoylamide; sodium salt;
6-morpholin-4-yl-pyridine-3-sulfonic acid 2-chloro-4-fluoro-benzoylamide; sodium salt;
6-morpholin-4-yl-pyridine-3-sulfonic acid 4-fluoro-2-trifluoromethyl-benzoylamide;
4-methoxy-3,4,5,6-tetrahydro-2H-[1,2']bipyridinyl-5'-sulfonic acid 2,4-dichloro-benzoylamide;
4-methyl-3,4,5,6-tetrahydro-2H-[1,2']bipyridinyl-5'-sulfonic acid 4-chloro-2-trifluoromethyl-benzoylamide;
6-azepan-1-yl-pyridine-3-sulfonic acid 4-chloro-2-trifluoromethyl-benzoylamide;
6-pyrrolidin-1-yl-pyridine-3-sulfonic acid 4-chloro-2-trifluoromethyl-benzoylamide; ammonium salt;
4-methoxy-3,4,5,6-tetrahydro-2H-[1,2']bipyridinyl-5'-sulfonic acid 4-chloro-2-trifluoromethyl-benzoylamide; ammonium salt;
6-(2,6-dimethyl-morpholin-4-yl)-pyridine-3-sulfonic acid 4-chloro-2-trifluoromethyl-benzoylamide;
6-thiomorpholin-4-yl-pyridine-3-sulfonic acid 4-chloro-2-trifluoromethyl-benzoylamide; ammonium salt;
4-methyl-3,4,5,6-tetrahydro-2H-[1,2']bipyridinyl-5'-sulfonic acid 2,4-dichloro-benzoylamide; ammonium salt;
4-methyl-3,4,5,6-tetrahydro-2H-[1,2']bipyridinyl-5'-sulfonic acid 2-chloro-4-fluoro-benzoylamide;
6-azepan-1-yl-pyridine-3-sulfonic acid 2-chloro-4-fluoro-benzoylamide;
6-pyrrolidin-1-yl-pyridine-3-sulfonic acid 2-chloro-4-fluoro-benzoylamide;
3-methyl-3,4,5,6-tetrahydro-2H-[1,2']bipyridinyl-5'-sulfonic acid 2-chloro-4-fluoro-benzoylamide;
6-thiomorphin-4-yl-pyridine-3-sulfonic acid 2-chloro-4-fluoro-benzoylamide;
6-azepan-1-yl-pyridine-3-sulfonic acid 2,4-dichloro-benzoylamide;
6-pyrrolidin-1-yl-pyridine-3-sulfonic acid 2,4-dichloro-benzoylamide;
6-thiomorphol in-4-yl-pyridine-3-sulfonic acid 2,4-dichloro-benzoylamide;
6-((2R,6S)-2,6-dimethyl-morpholin-4-yl)-pyridine-3-sulfonic acid 4-chloro-2-trifluoromethyl-benzoylamide;
3-methyl-3,4,5,6-tetrahydro-2H-[1,2']bipyridinyl-5'-sulfonic acid 2,4-dichioro-benzoylamide;
6-(2,6-dimethyl-morpholin-4-yl)-pyridine-3-sulfonic acid 2,4-dichloro-benzoylamide;
6-((2R,6S)-2,6-dimethyl-morpholin-4-yl)-pyridine-3-sulfonic acid 2,4-dichioro-benzoylamide;
4-methyl-3,4,5,6-tetrahydro-2H-[1,2']bipyridinyl-5'-sulfonic acid 4-fluoro-2-trifluoromethyl-benzoylamide;
6-azepan-1-yl-pyridine-3-sulfonic acid 4-fluoro-2-trifluoromethyl-benzoylamide;
6-pyrrolidin-1-yl-pyridine-3-sulfonic acid 4-fluoro-2-trifluoromethyl-benzoylamide; and
6-thiomorphin-4-yl-pyridine-3-sulfonic acid 4-fluoro-2-trifluoromethyl-benzoylamide.

9. A compound according to claim 6 wherein:

R² is selected from the group consisting of: chlorine and trifluoromethyl; and

R³ is selected from the group consisting of: fluorine and chlorine.

10. A process for the preparation of a compound according to claim 1 comprising reacting acompound of formula IIIa,

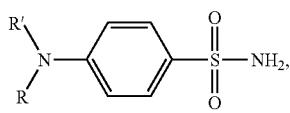

formula IIIa wherein R and R' are as defined in claim 1, with a compound of formula V,

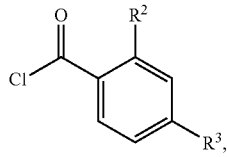

formula V wherein R² and R³ are as defined in claim 1.

11. A compound according to claim 1, wherein said heterocycle is selected from the group consisting of: morpholine, thiomorpholine, pyrrolidine, and azepane.

12. A compound according to claim 11 wherein said heterocycle is morpholine.

\* \* \* \* \*

UNITED STATES PATENT AND TRADEMARK OFFICE
CERTIFICATE OF CORRECTION

PATENT NO. : 7,625,896 B2  Page 1 of 1
APPLICATION NO. : 11/594297
DATED : December 1, 2009
INVENTOR(S) : Kling et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 37 days.

Signed and Sealed this

Sixteenth Day of November, 2010

David J. Kappos
*Director of the United States Patent and Trademark Office*